(12) United States Patent
Seifert et al.

(10) Patent No.: US 8,858,598 B2
(45) Date of Patent: Oct. 14, 2014

(54) LATERAL SPINOUS PROCESS SPACER WITH DEPLOYABLE WINGS

(75) Inventors: Jody L. Seifert, Birdsboro, PA (US); Michael L. Boyer, II, Phoenixville, PA (US); David C. Paul, Phoenixville, PA (US); Noah Hansell, King of Prussia, PA (US); Mark Adams, Honey Brook, PA (US)

(73) Assignee: Globus Medical, Inc., Audubon, PA (US)

( * ) Notice: Subject to any disclaimer, the term of this patent is extended or adjusted under 35 U.S.C. 154(b) by 146 days.

(21) Appl. No.: 13/211,945

(22) Filed: Aug. 17, 2011

(65) Prior Publication Data
US 2012/0029565 A1    Feb. 2, 2012

Related U.S. Application Data

(63) Continuation of application No. 12/334,266, filed on Dec. 12, 2008, now Pat. No. 8,021,393.

(51) Int. Cl.
*A61B 17/70* (2006.01)
*A61B 17/34* (2006.01)
*A61B 19/00* (2006.01)
*A61F 2/30* (2006.01)

(52) U.S. Cl.
CPC ..... *A61B 17/7065* (2013.01); *A61F 2250/0098* (2013.01); *A61B 17/3421* (2013.01); *A61B 17/3468* (2013.01); *A61B 2017/3433* (2013.01); *A61B 19/54* (2013.01); *A61F 2002/3008* (2013.01)
USPC .......................................... 606/248; 606/249

(58) Field of Classification Search
USPC ............. 606/246, 248, 249; 623/17.11–17.16
See application file for complete search history.

(56) References Cited

U.S. PATENT DOCUMENTS

| | | | |
|---|---|---|---|
| 8,317,864 B2* | 11/2012 | Kim | 623/17.11 |
| 2008/0065214 A1 | 3/2008 | Zucherman et al. | |
| 2008/0071380 A1* | 3/2008 | Sweeney | 623/17.16 |
| 2008/0177391 A1* | 7/2008 | Mitchell et al. | 623/17.16 |
| 2008/0243250 A1* | 10/2008 | Seifert et al. | 623/17.16 |

* cited by examiner

*Primary Examiner* — Pedro Philogene
*Assistant Examiner* — Christina Negrellirodrigue

(57) ABSTRACT

Interspinous process implants are disclosed. Also disclosed are systems and kits including such implants, methods of inserting such implants, and methods of alleviating pain or discomfort associated with the spinal column.

8 Claims, 26 Drawing Sheets

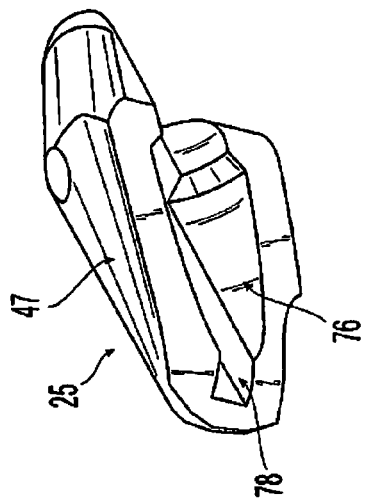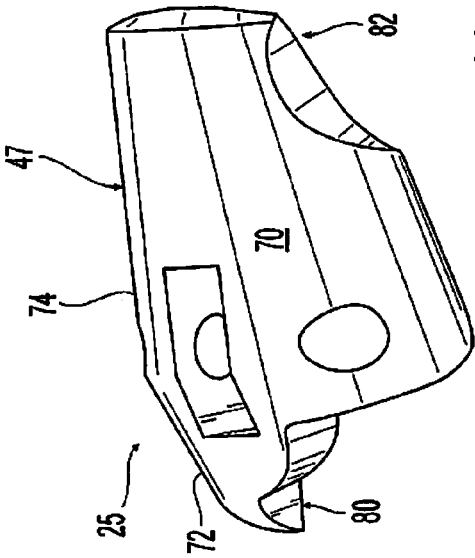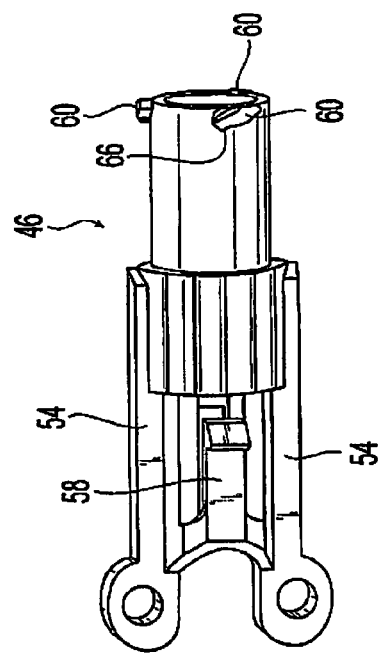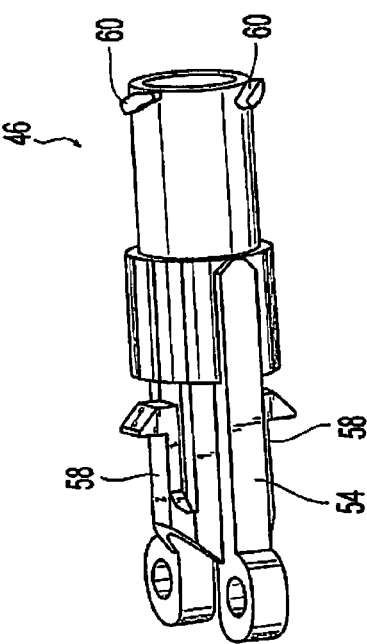

LATERAL SPINOUS PROCESS SPACER WITH DEPLOYABLE WINGS

CROSS REFERENCE TO RELATED APPLICATIONS

This patent application is a continuation application claiming priority to U.S. patent application Ser. No. 12/334,266 filed on Dec. 12, 2008 now U.S. Pat. No. 8,021,393, the entire contents of which are incorporated by reference.

FIELD OF THE INVENTION

The present invention is generally directed to intervertebral or interspinous process implants, systems and kits including such implants, methods of inserting such implants, and methods of treating spinal stenosis or for alleviating pain or discomfort associated with the spinal column.

BACKGROUND OF THE INVENTION

Occurrences of spinal stenosis are increasing as society ages. Spinal stenosis is the narrowing of the spinal canal, lateral recess or neural foramen, characterized by a reduction in the available space for the passage of blood vessels and nerves. Clinical symptoms of spinal stenosis include extremity pain, radiculopathy, myelopathy, sensory or motor deficit, bladder or bowel dysfunction, and neurogenic claudication. Pain associated with such stenosis can be relieved by surgical or non-surgical treatments, such as medication, physical therapy, back braces and the like. While spinal stenosis is generally more prevalent of the elderly, it can occur in individuals of all ages and sizes.

There is a need for implants that may be placed between spinal processes for minimally or less invasive surgical treatment of spinal stenosis and, in particular, for implants that may be installed unilaterally and/or without removal of the supraspinous ligament.

SUMMARY OF THE INVENTION

Certain embodiments of the present invention are generally directed to minimally or less invasive implants, in particular, interspinous process implants or spacers. Other embodiments of the invention are further directed to systems and kits including such implants, methods of inserting such implants, and methods of alleviating pain or discomfort associated with the spinal column.

Some embodiments of the present invention provide spacers or implants and methods for relieving pain and other symptoms associated with spinal stenosis, by relieving pressure and restrictions on the blood vessels and nerves. Such alleviation of pressure may be accomplished in the present invention through the use of an implant placed between the spinous process of adjacent vertebra.

BRIEF DESCRIPTION OF THE DRAWINGS

The invention will be more readily understood with reference to the embodiments thereof illustrated in the attached figures, in which:

FIGS. 10-11 are perspective views of a wing member of the implant of FIG. 1;

FIGS. 12-13 are perspective views of a barrel insert of the implant of FIG. 1;

DETAILED DESCRIPTION OF THE ILLUSTRATED EMBODIMENTS

Figure 1:
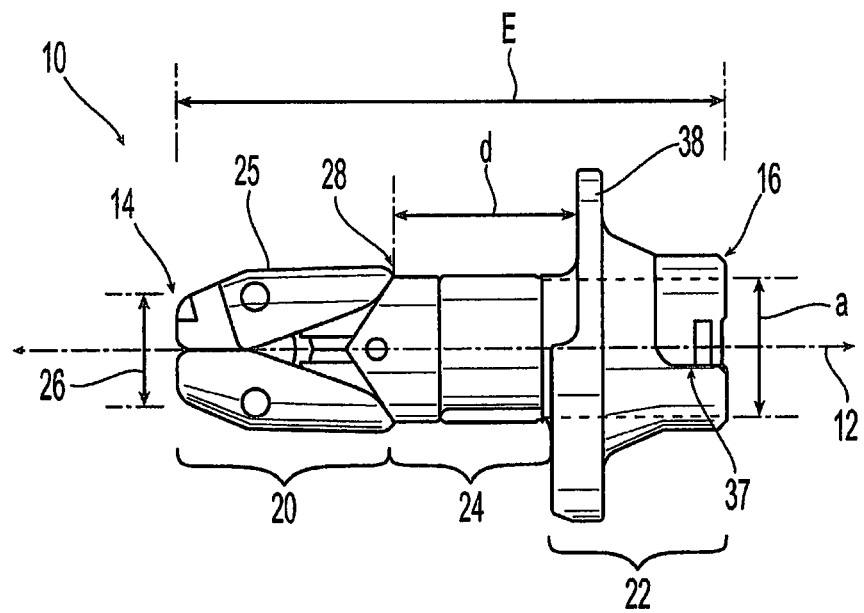
FIG. 1 is a side perspective view of one embodiment of an implant according to the invention for creating, increasing, or maintaining distraction between adjacent spinous processes.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Implants

Some embodiments of the present invention are directed to minimally or less invasive implants, in particular, interspinous process spacers. Implants in accordance with the invention may come in many shapes and sizes. The illustrative embodiments provided herein-below provide guidance as to the many types of implants that may be advantageously used in accordance with the present invention. In particular, the implants are adapted such that their insertion technique (including methods of the present invention) is minimally or less invasive, and generally simpler, and/or safer than those installed in open or more invasive techniques. According to one aspect, implants according to the present invention may be advantageously inserted into a patient as an out-patient procedure.

Embodiments of the present invention include implants adapted to be placed between first and second adjacent spinous processes. The implants may be adapted such that after insertion of an implant into a patient, a portion of the implant maintains a desired amount of distraction or spacing between two adjacent spinous processes. The implants or portions thereof that substantially maintain a desired spacing between spinous processes are also referred to herein as "spacers." In various embodiments described herein, the implants may include spinous process support surfaces, indented portions or saddle portions spaced apart by a distance (a) (FIG. 1), which generally corresponds to a desired distance for distraction or spacing of two adjacent spinous processes. Other embodiments similarly provide a desired distance for distraction or spacing of two adjacent spinous processes. Depending on the material and/or design of the implant, the desired distraction or spacing distance may vary somewhat after insertion, for example if a patient moves its spine into a position that causes further distraction. For example, in certain embodiments the implant may be resiliently compressible or expandable in the cranial-caudal direction such that the implant may support and or adjust to dynamic movement of the spine. Although not depicted in the figures discussed below, it is contemplated that embodiments of the present invention may be extended to provide distraction or spacing of more than two adjacent spinous processes.

Implants according to the present invention may be adapted to be inserted between a first and second spinous process at any region in the spine. Although typically implants according to the present invention may be inserted in the lumbar region, it is contemplated that it is possible to configure inserts according to the present invention for insertion into other regions such as for example, the thoracic or cervical region. In general, implants according to the invention may have varying profiles when viewed in a sagittal plane. In this regard, the implants can have varied cross-sectional shapes to conform to the varied anatomical shapes of the interspinous spaces of the spine.

Certain embodiments of implants of the invention may secure themselves in place without a supplemental attachment mechanism or fastening device attached directly to a spinous process or other portion of the spine. Alternatively, implants in accordance with the invention may be attached to one or more spinous processes or other portion of the spine, or may attach to itself in such a manner as to secure the implant between two adjacent spinal processes. By way of example, implants in accordance with the present invention may be attached to one or both spinous processes or other portion of the spine by one or more pins, screws, wires, cables, straps, surgical rope, sutures, elastic bands, or other fastening devices. Other exemplary implants, attachment mechanisms, and methods that may be utilized are disclosed in U.S. patent application Ser. Nos. 11/366,388; 11/691,357; and 12/107,222, the entire contents of which are incorporated herein by reference. "Securing" implants between spinous processes, does not require that the implant not move at all, but rather means that the implant does not move so far away from between the spinous processes that it does not perform the function of maintaining a desired distraction distance or space between the adjacent spinous processes.

Implants in accordance with the present invention may be secured between spinous processes by methods other than using a fastening device. For example, according to certain embodiments, implants in accordance with the present invention may be secured in place with respect to spinous processes by mechanical forces resulting from the design of the implant, including the shape itself. Exemplary implants may also be secured to spinous processes, by surface modifications to portions of the implant, such as to create frictional forces or other bonds between the implant and spinous processes. Such surface modifications may include mechanical modifications to the surface and/or one or more coatings. Exemplary coatings which may be utilized include, but are not limited to, titanium plasma sprays and chrome sprays or the like. Such mechanical forces and/or surface modifications may be utilized in addition to, or in place of various other attachment methods described herein.

Figure 5:
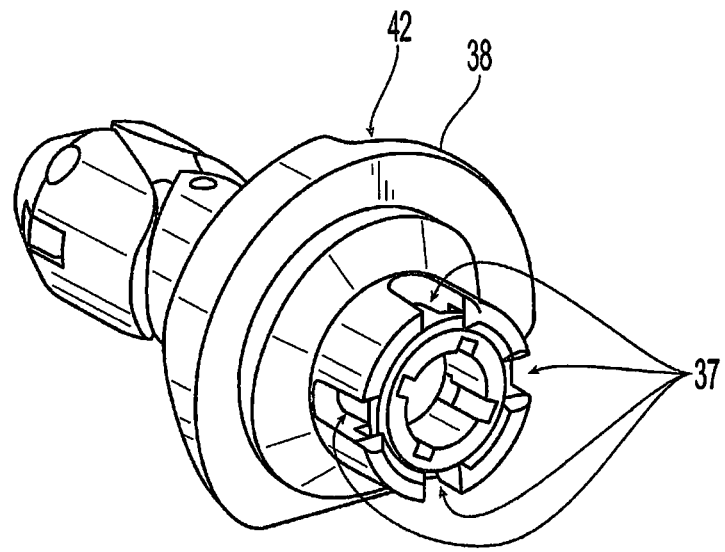
FIG. 5 is a proximal perspective view of the implant of FIG. 1 shown in a first position.
Figure 6:
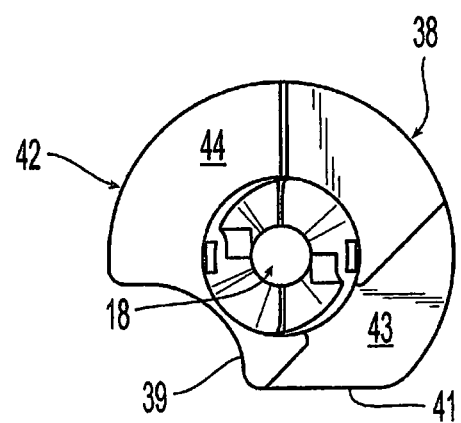
FIG. 6 is a distal end view of the implant of FIG. 1 shown in a first position.
Figure 7:
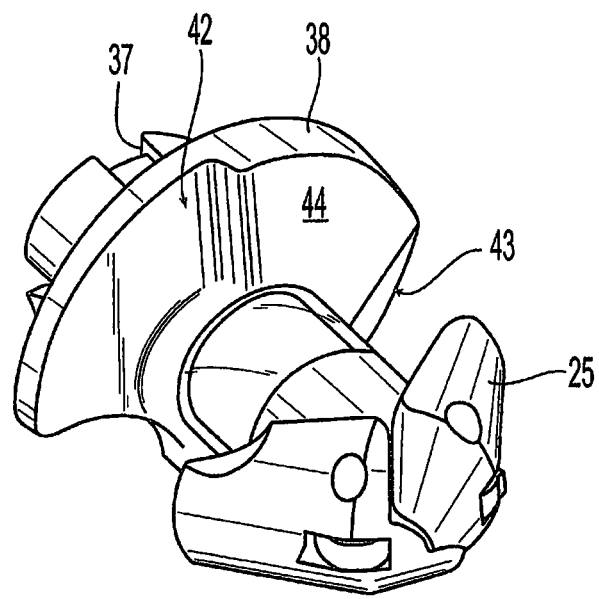
FIG. 7 is a distal perspective view of the implant of FIG. 1 shown in a second position.

Referring now to FIGS. 1-15, one exemplary embodiment of an implant 10 according to the invention is shown for creating, increasing, or maintaining distraction between adjacent spinous processes. In general, implant 10 is adapted and configured to be placed between adjacent spinous processes. For example, referring to FIGS. 57-58, a posterior and side perspective view, respectively, of implant 10 is shown in implanted positions between to two adjacent spinous processes 5. As best seen in FIGS. 1-8, implant 10 generally comprises an elongate member extending laterally along axis 12 from a distal or first lateral end 14 to a proximal or second lateral end 16. In one embodiment, implant 10 may be cannulated with a central cannula or opening 18 extending along axis 12. One skilled in the art may appreciate that, in operation, cannulation 18 may facilitate advancement, travel, or delivery to an implant location over a guidewire. In alternate embodiments, however, implant 10 may not be cannulated but may be generally solid. According to one embodiment, implant 10 may comprise a multi-piece body with a general arrow or barbell-like shape, and generally includes a leading end portion, first end portion, or distraction portion 20 adjacent first end 14, a second end portion or trailing end portion 22 adjacent second end 16, and a central support portion or saddle portion 24 disposed between the leading and trailing end portions 20, 22. As best seen in FIG. 1, support portion 24 may have a height (a) and width (d), and the implant may have an overall length (E). As best seen in FIGS. 5 and 7, in one embodiment, saddle portion 24 has a generally circular profile or perimeter when viewed perpendicular to axis 12. In alternate embodiments, however, saddle portion need not have a circular cross-sectional profile and the cross-sectional profile may vary along its length. For example, in one exemplary embodiment, central support portion 24 may have a polyganol cross-sectional profile.

Trailing end portion 22 adjacent second end 16 may comprise a shoulder or flange 38 with generally frustoconical, wedged, or tapered trailing portion narrowing along axis 12 from a major or large diameter or radial dimension adjacent central support portion 24 toward the second end 16. Those skilled in the art will appreciate that such a tapered feature may be desirable to minimize wear and trauma with adjacent soft tissue and/or bone when implant 10 is installed in a patient. In one embodiment trailing end portion 22 may be generally symmetrical to distraction portion 20 with generally similar lateral length and taper. In alternate embodiments, however, the trailing end portion 22 need not be symmetrical whatsoever and may have any shape irrespective of the dimension of distraction portion 20.

Figure 57:
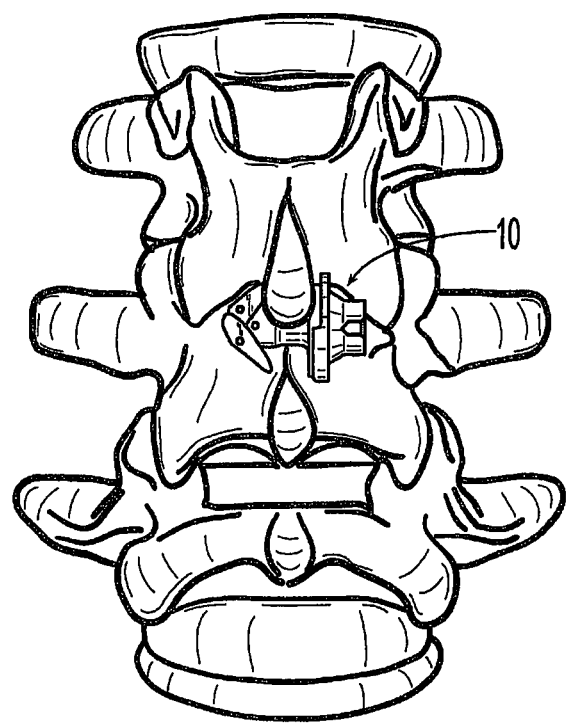
FIGS. 57-58 depict perspective views of the implant of FIG. 1 shown in an implanted position.
Figure 58:
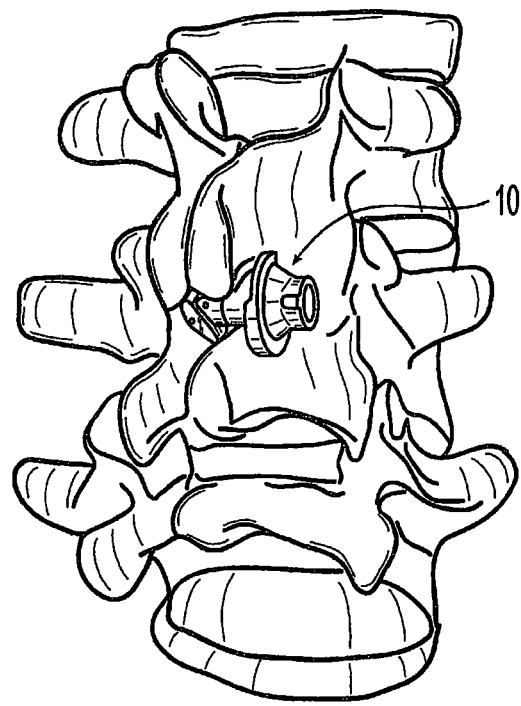

Flange 38 generally defines a sidewall adjacent the central support portion 24 configured and dimensioned to be positioned adjacent and/or contact a lateral side of a spinous process when implanted. According to several of the embodiments depicted herein, flange 38 may have numerous features to accommodate the physical anatomy of the spine when implanted in a patient. In one embodiment, shoulder portion 38 generally extends between about 180 degrees and 270 degrees around axis 12, leaving a portion of the periphery without a sidewall 44 adjacent the support portion 24. As best seen in FIG. 6, a crescent or arcuate shaped cutout portion 39 may be disposed or formed along the perimeter of flange 38 to accommodate the lamina and/or lamina spinous process junction region of the vertebra and to facilitate the anterior placement of the implant thereagainst. A flat perimeter portion 41 may be provided to minimize the flange along the anterior side of the implant such that when implant 10 is implanted in a patient, the implant may be positioned as anterior as possible. As best seen in FIGS. 57-58, in one variation, the crescent shaped cutout portion 39 is configured and dimensioned to be positioned adjacent a lamina portion of a superior vertebrae when installed. In another variation, flange 38 may have a thinner section 42 on the upper portion of flange 38 adjacent cutout 39. As best seen in FIGS. 57-58, such a thin section 42 may be configured and dimensioned to accommodate abutting placement against the superior spinous process when implanted. Similarly, a lower portion of flange 38 may have a chamfer 43 or angled inner surface to accommodate a lamina portion of an inferior vertebrae when installed.

Figure 2:
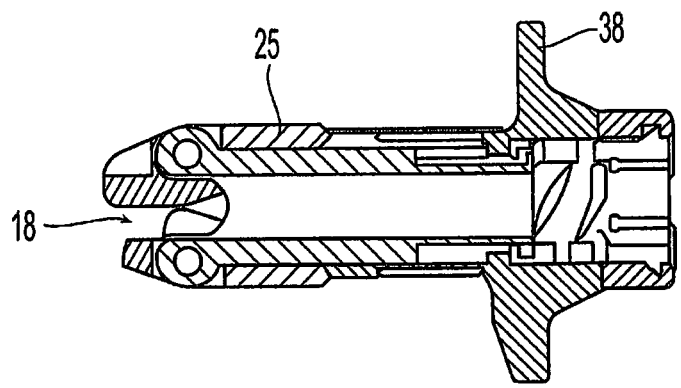
FIG. 2 is a cross-sectional view of the implant of FIG. 1 shown in a first position.

According to one variation, leading end portion 20 generally comprises a pair of wing members 25 movable from a first position, shown in FIGS. 1-2 and 5-6, to a second position, shown in FIGS. 3-4 and 7-8. Referring to FIGS. 1-2, wing members 25 are depicted in a first or closed position and are configured and dimensioned to facilitate lateral insertion between adjacent spinous processes. In the first position, the exterior of wing members 25 are gradually tapered from a narrow portion adjacent end 14 to a wider shoulder section 28 adjacent support portion 24. In this regard, when in the closed or first position, wing members 25 generally form a distraction portion 20 having a frustoconical, wedged, or tapered shape widening along axis 12 from a minor diameter 26 adjacent the first end 14 to shoulder 28 adjacent central support portion 24. In one variation, shoulder 28 may be generally co-extensive with the central support portion 24 such that a generally smooth transition may occur as one or more spinous processes contacts and or slides along exterior wing surface during insertion of implant 10 into the interspinous space. In alternate embodiments, shoulder 28 may protrude longitudinally or radially beyond the support portion 24 when wings 25 are in the first or closed position such that an overdistraction of the spinous processes may occur during insertion of implant 10 into the interspinous space. One skilled in the art may appreciate that with the wing members in the first or closed position, such a configuration may facilitate unilateral insertion between adjacent spinous processes, i.e. implant 10 may be inserted between adjacent spinous processes from only one side.

Figure 3:
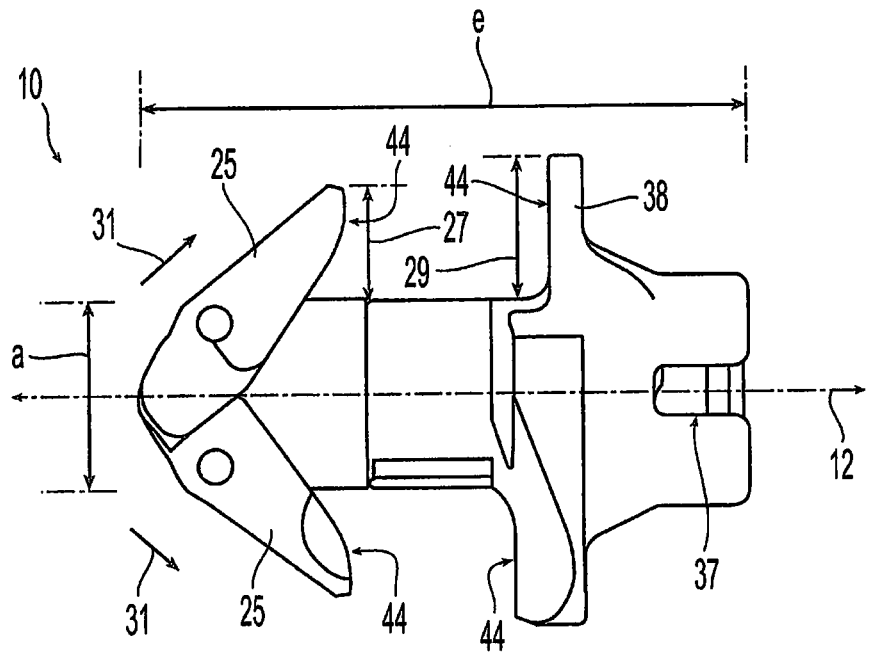
FIG. 3 is a side perspective view of the implant of FIG. 1 shown in a second position.
Figure 4:
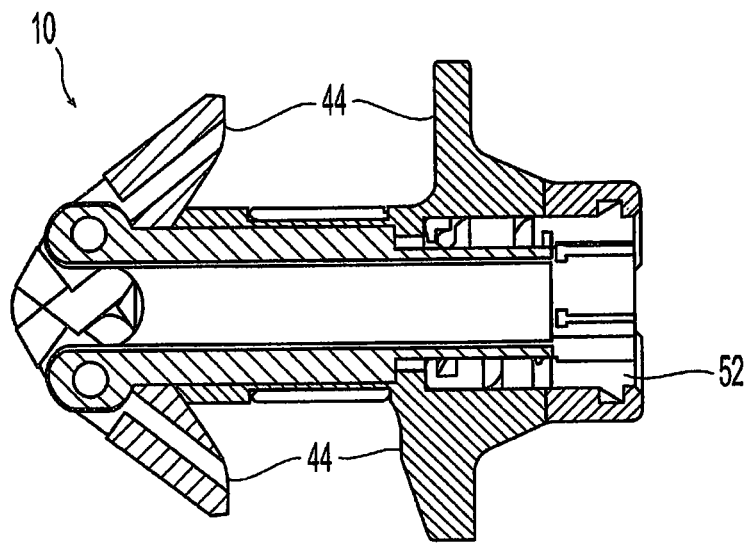
FIG. 4 is a cross-sectional view of the implant of FIG. 1 shown in a second position.

Referring now to FIGS. 3-4, implant 10 is shown with wing members 25 disposed in a second, expanded, or open position. In this regard, during installation, wing members 25 are configured to remain in the first or closed position and when implant 10 is installed in an implanted position, wing members 25 may be selectively moved into the second position, as shown in FIGS. 3-4. In the second position, the wing members 25 generally protrude or extend radially beyond support portion 24 to a greater extent than in the first position. In this regard, the wing members 25 create a flange, or lateral sidewall portion 44 opposite sidewall 44 of shoulder 38 of trailing end 22. In this position and when implanted, the adjacent spinous processes may be maintained between the wing members 25 and the trailing end portion 22 such that the wall sections 44 may serve to limit or block movement of implant 10 along axis 12 and/or dislodgement from the interspinous space. In this regard, when viewed from the side, as seen in FIG. 3, implant 10 may appear to have a general H-like shape or a barbell-like shape, with the lateral sides 20, 22, being longitudinally spaced a distance 27, 29, respectively beyond central support portion 24. In one variation, distances 27, 29 do not need to be equal. According to one embodiment, lateral sides 20, 22 may be spaced a distance 27, 29 between about 1 mm and about 6 mm from the support portion 24. In one particular embodiment, distances 27, 29 is about 1 mm. In another embodiment, distance 23 is about 2 mm and distance 25 is about 3 mm. As shown in FIG. 3, when implant 10 is in the second position, the overall length of implant 10 decreases to a length (e) shorter than the overall length (E) of the implant 10 in the first position. In this regard, such a shortening of the implant along axis 12 is generally caused by the movement of wing members 25 in the direction of arrows 31 shown in FIG. 3.

Figure 8:
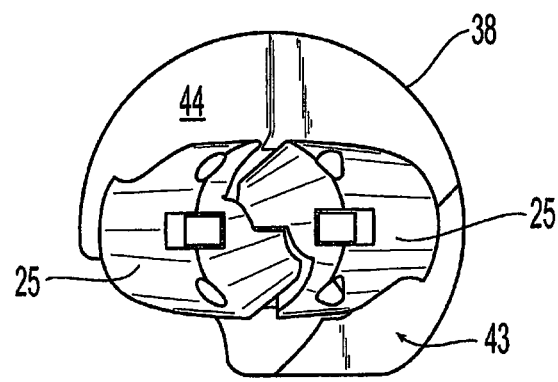
FIG. 8 is a distal end view of the implant of FIG. 1 shown in a second position.

Referring now to FIG. 8, in the second position, wings 25 may abut and/or intermesh at the first end 14. Those skilled in the art may appreciate that when in such a configuration, the wing members themselves may function to resist any further rotation or sliding movement of wing members 25 with respect to central portion 24 during deployment, and may provide additional support to resist lateral forces that may be placed on the wings once deployed.

Figure 9:
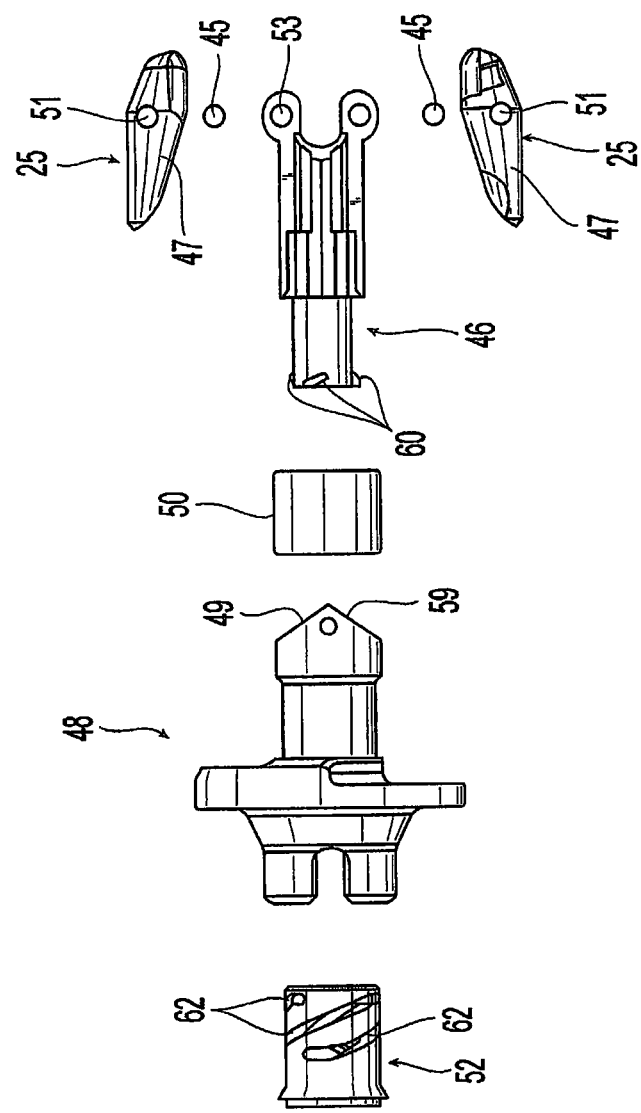
FIG. 9 is an exploded view of the implant of FIG. 1.

Referring to FIG. 9, an exploded view of one embodiment of implant 10 is shown. According to one variation, implant 10 may comprise a multi-piece device generally having wing members 25, pivot pins 45, a barrel insert 46, a central body 48, a flexible bumper member 50, and a rotatable insert 52. In alternate embodiments, more or less components may be provided to achieve similar results. In general, each wing member 25 may comprise a cantilevered body or pivot body 47 freely rotatable or pivotable about a pivot point or pin 45 extending transversely through the wing member via hole 51 of wings 25. Pins 45 are generally mounted to and/or extend through holes or openings 53 provided at the distal end of barrel insert 46 such that wing members 25 may pivot or rotate with respect to barrel insert 46 about the distal end thereof. Central body 48 has an annular shape with a chamfered or angled tip portion 49 at its distal end to facilitate sliding and/or rotative movement of wing members 25 thereagainst.

Figure 14:
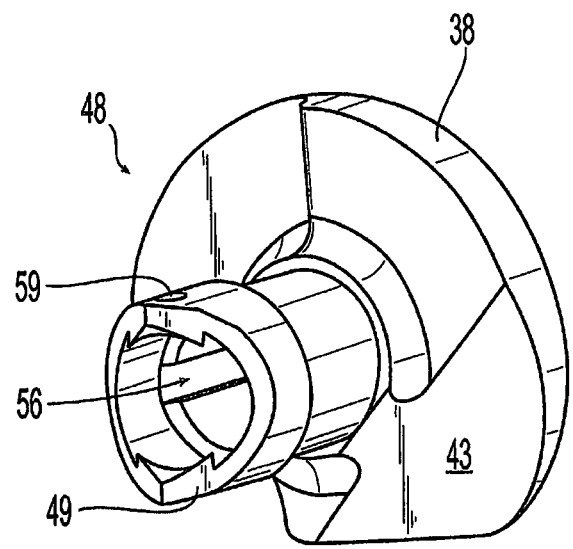
FIG. 14 is a perspective view of a central body of the implant of FIG. 1.

Barrel insert 46 is configured and dimensioned to be received within central body 48 and according to one variation may be keyed with respect to the central body such that barrel insert 46 may translate linearly or move along axis 12 but is prevented from rotating with respect to the central body 48. In this regard, barrel insert 46 may have ears or ledge portions 54 along a portion of its length configured and dimensioned to fit or ride within grooves 56 provided within the interior of central body 48 (FIG. 14). A pair of cantilevered flexible arm sections 58 may be provided along a portion of its length to facilitate removal of barrel insert 46 from central body 48 after assembly. In this regard, when wing members 25 of implant 10 are in a first position, such as shown in FIG. 2, a removal tool (not shown) may be inserted through openings 59 to depress arms 58 and central body 48 may be slidably removed from the back or proximal end of barrel insert 46. As shown in FIGS. 12-13, one or more prongs or protrusions 60 may extend radially outward from the proximal or back end of barrel insert 46 to engage with rotatable insert 52. In one variation, three protrusions 60 may be angularly spaced about the proximal end of barrel 46.

Figure 15:
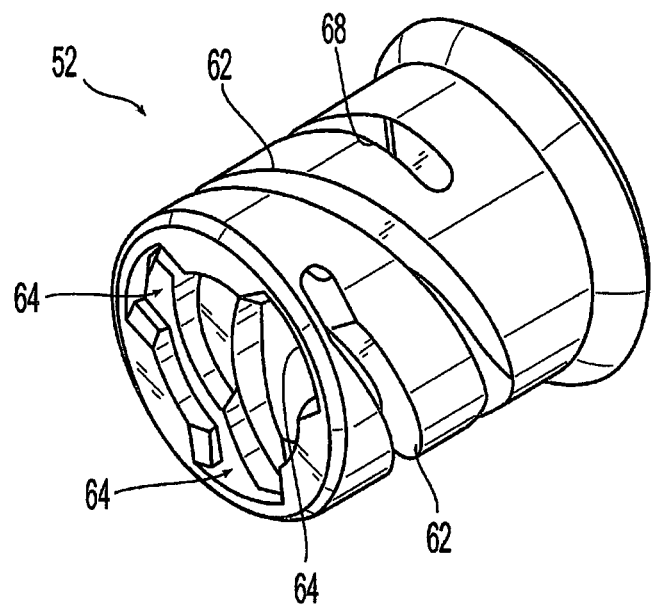
FIG. 15 is a perspective view of a rotatable insert of the implant of FIG. 1.
Figure 16:
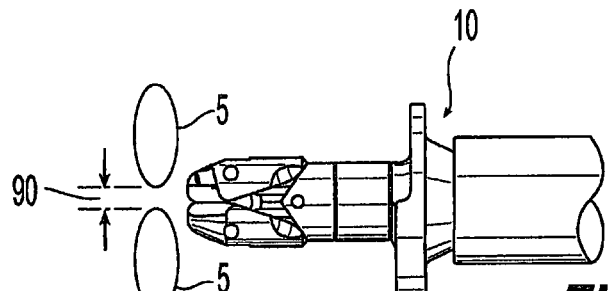
FIG. 16-20 are side views demonstrating various steps according to one embodiment of a method of installation of the implant of FIG. 1.
Figure 17:
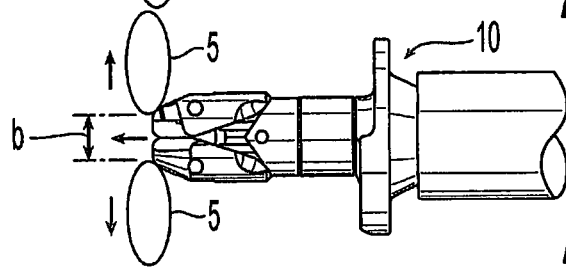
Figure 18:
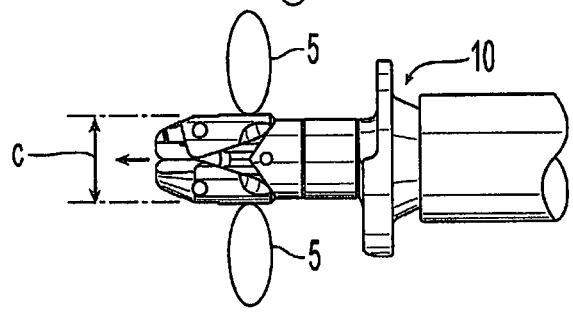
Figure 19:
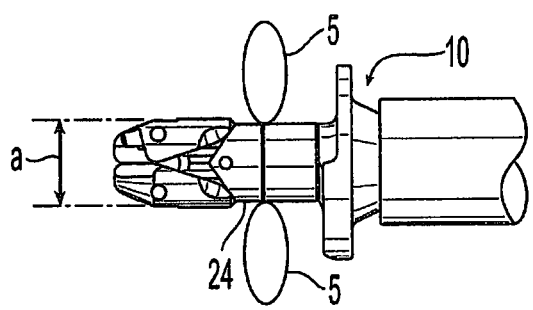

A rotatable insert 52 may be provided adjacent the proximal or second end 16. As shown in FIG. 15, insert 52 may have one or more spiral grooves 62 to accommodate protrusions 60 at the proximal or back end of barrel insert 46. In this regard, bayonet like openings 64 may be provided at the distal end of insert 52 to accommodate protrusions 60 during assembly. Rotatable insert 52 may be axially fixed within central body 48 yet freely rotatable with respect thereto. When assembled, the back or proximal end of barrel 46 may ride in groove 62 of rotatable insert 52 and when insert 52 is rotated with respect to the central body 48, the barrel insert 46 may be drawn or moved in the proximal direction along axis 12 towards the second end 16. The pivot pins 45 located at the distal end of barrel insert 46 will be correspondingly drawn or moved in the proximal direction along axis 12 causing the pivot axis 51 of wing members 25 to move and causing the wing members 25 to engage the central body 48. In this regard, wing members 25 are configured and dimensioned to be pivotable about a moving axis of rotation. In one variation, spiral groove 62 may extend one quarter of a revolution or 90 degrees about rotatable insert 52 such that a user may cause the wing members to completely deploy upon one quarter turn of rotatable insert 52.

According to one embodiment, protrusions 60 may have a rounded section or bump 66 along its periphery to facilitate contact and/or engagement with a correspondingly shaped indentation 68 provided along the profile of groove 62. In this regard, when bump 66 engages indentation 68 a user may be provided with tactile and/or audible feedback indicating the position of the barrel with respect to the rotation insert. In one variation, indentation 68 is proved adjacent the proximal end of groove 62 such that a user may be indicated that barrel 46 is drawn back proximally as far as possible and in accord therewith, the wing members 25 are completely deployed. Those skilled in the art may appreciate the desirability of such a feature, especially when an implant may be used percutaneously, minimally invasively, or in any procedure with limited ability for direct visualization of the implant during implantation. It may be appreciated that such a bump and indentation feature may also serve as a frictional rotation lock once engaged since a slightly greater rotational force must be applied to overcome the frictional engagement when reversing the rotational direction of insert 52. In this regard, the rotational lock may limit and/or prevent wing members 25 from undesirably moving back into the first or collapsed position once implant 10 is implanted in a patient.

As best seen in FIGS. 10-11, one embodiment of a wing member 25 according to the invention is shown having a generally shell-like shape. In one variation, the exterior or outwardly facing surface 70 of wing members 25 is generally convex and may have a first ramped or tapered section 72 and a generally flatter second ramped tapered section 74. In this regard, such a smooth, ramped, and/or tapered exterior generally facilitates direct lateral insertion into an interspinous space by a straight axial pushing force along the direction of axis 12. In another variation, the interior, underside, or inwardly facing surface 76 of wing members 25 is generally concave and may include a groove 78 along its length to accommodate sliding movement with respect to central body 48. According to one variation, wing members 25 may be moved toward the second position by moving barrel insert 46 in the proximal direction along axis 12. When wing members 25 are moved from the first position to the second position, the underside 76 of each wing member 25 is generally rotated or moved to face the central support portion 24 and the undersurface 76 forms the sidewall section 44. In this regard, wings 25 may be attached to implant 10 such that when in a second position, the interior or inwardly facing surface 76 is generally perpendicular to support portion 24 to create a larger lateral barrier, blocking portion, or wall 44 adjacent central support portion 24.

In operation, implant 10 may be first inserted over a guidewire into a space between spinous processes. In this regard, when implant 10 is advanced over a guidewire, the guidewire generally extends within the central cannula 18 and contacts the tail portion 80 of each wing member and the tail portion 80 is forced radially outward, causing the tip portion 82 to pivot inward and/or remain in the first position. One skilled in the art may appreciate that utilizing such a configuration, the wing members 25 may remain in a first position to facilitate implantation over a guidewire and then once the guidewire is removed, the wing members may be selectably moved to the second position to form a larger lateral barrier, wall, or blocking portion adjacent central support portion to limit or reduce the possibility of lateral migration of implant 10 in the body.

Once installed into the desired position, the guidewire may be removed and the wing members may be deployed or moved to the second position by rotating insert 52 with respect to central body 48. When rotation insert 52 is turned with respect to central body 48, an axial force is transmitted to the barrel insert to move the barrel insert 46 in the proximal direction to draw the pivot pins toward the second lateral end 16. A tip portion 82 of one side of the wing body 47 contacts central body 48 to cause an opposite tail portion 80 of each wing member 25 to pivot about point 51 toward the second position. The inner tail surfaces 76 of wing members 25 ride along the chamfered tip 49 of central body 48 which acts a ramp to force the wings to rotate about pivot point 51 and swing outward and move to the second position. In alternate embodiments, alternative mechanisms may be utilized to achieve the aforementioned result. For example, in one alternative a torsion spring may be positioned adjacent pivot point 51 to bias the wing members 25 toward the second position.

Also, in alternative embodiments, the shapes and dimensions of wing members may be altered as desired.

According to one aspect of this embodiment explained above, the wing members 25 swing outward with the tips 82 generally moving away from the center of the implant. In this regard, the tips 82 are generally configured to move up and under any tissue or muscle that may be abutting against the adjacent spinous processes. Those skilled in the art may appreciate the advantageous nature of such a feature. In particular, such outwardly swinging wing movement may be appreciated to require less activation force and facilitate tissue preservation as compared to alternative wing movements. For example, certain inward swinging movements could easily cause tissue to become trapped between the implant sidewalls and the spinous process and/or cause tissue damage.

Referring to FIG. 3, in one embodiment, one or more sockets, grooves or indentations 37 may be provided on the proximal end of implant 10 and angularly spaced about the periphery thereof to receive an installation or driving tool such as a crucifix shaped driver tool. In alternate embodiments, any other known rotational driving tools and engagement means may also be used, including but not limited to, a flat driver, a star shaped driver, or a threaded driver, among others. As best seen in FIG. 5, indentations 37 may be spaced along the perimeter of implant 10 to facilitate insertion with a cannulated driver tool over a guidewire extending through cannula 18. The proximal end of rotatable insert 52 may have similarly spaced grooves around the proximal perimeter thereof which may be accessed by a concentric rotation driving tool. In this regard, rotatable insert 52 may be rotated relative to central body 48 to, for example, deploy wing members 25. In one variation, a laterally fixed engagement between the tool and the implant may be provided so that the implant does not dislodge from the trailing end and may efficiently transfer the rotational forces applied on the tool to the implant during installation. One skilled in the art may appreciate that a threaded connection may also facilitate the removal of implant 10 from the body of a patient should a surgeon so desire.

In some embodiments, all or a portion of implant 10 may be resiliently compressible or expandable in the cranial-caudal direction such that the implant may support and or adjust to dynamic movement of the spine. For example, according to one embodiment, a flexible bumper member 50 may be provided to at least partially cushion the compression of adjacent spinous processes. In one variation, the bumper member 50 may comprise a cylindrical sleeve provided to extend around the periphery of central support portion 24. In some embodiments, the bumper member may be integrated into the support portion and in alternate embodiments the bumper member may be fit over the support portion. In one variation, the bumper member may be made from a biocompatible polyurethane, elastomer, or other similar material. In still other embodiments, implant 10 may be made from varying materials along its length, such that for example the central support portion may be made from a resilient material, such as polyurethane, elastomer or the like, and the end portions may be made from a rigid material, such as titanium or the like.

Figure 20:
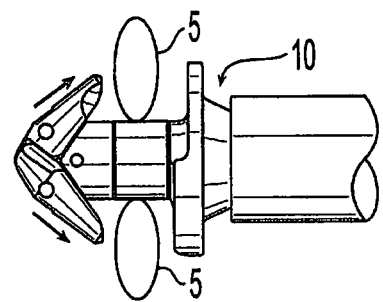

The implant itself may serve to dilate or distract the spinous processes as it is being inserted and/or after insertion. For example, in embodiments in which the implant is similar to that depicted in FIGS. 1-15, the first end 14 of implant 10 may be initially inserted or advanced laterally between compressed adjacent spinous processes as shown in FIGS. 16-20, for example. The supraspinous ligament may or may not be removed. In an initial pre-implantation condition, shown in FIG. 16, the adjacent spinous processes 5 may be compressed or narrowly spaced such that the initial space or longitudinal distance 90 between the processes may be about equal to or slightly larger or smaller than distance (b) of implant 10. During lateral insertion of the implant, one or more ramp or tapered surfaces or portions of the implant may contact one or both of the spinous processes 5 and may initially distract the processes a distance (b). As the implant is advanced laterally, the ramp or tapered shape of the distraction portion may distract the spinous processes further apart from one another, until the implant is advanced laterally into an implanted position (FIGS. 19-20) and the spinous processes are fitted into the central support portion 24 of the implant 10. In operation, the ramp surfaces engage the adjacent spinous processes as the implant is laterally advanced to act or perform in a cam-like manner to translate the lateral force to separate the spinous processes in the longitudinal or cranial-caudal direction as the implant is advanced. The maximum distraction of spinous processes by the implant 10 is distance (c) depicted in FIG. 18. According to one embodiment, distance (c) is greater than distance (a) such that the spinous processes 5 may be slightly "over distracted" during installation. In this regard, one skilled in that art may appreciate that such an over distraction may facilitate enhanced tactile feedback to a surgeon during installation as the spinous processes drop into the central support portion to signify a desired lateral placement in the patient with the spinous processes positioned within the central support portion. Once the implant is laterally advanced to the position shown in FIG. 19, the flange 38 of trailing end portion 22 may contact and/or abut the lateral side of the spinous processes to prevent further lateral translation and rotation insert 52 of implant 10 may be subsequently rotated about one quarter turn or about 90 degrees to deploy the wing members 25 into the final implantation position as shown in FIG. 20. In this regard, in the final implantation position, the shoulder wall sections 44 may contact the lateral sides of the spinous processes to limit or block movement of the implant along axis 12 and/or dislodgement from the interspinous space. Also, once the implant is implanted and after the spinous processes are fitted into the central support portion 24, the implant may maintain the spinous processes in a distracted or spaced condition, for example where the distance (a) of the implant is greater than a pre-implantation distance between the spinous processes.

Figure 21:
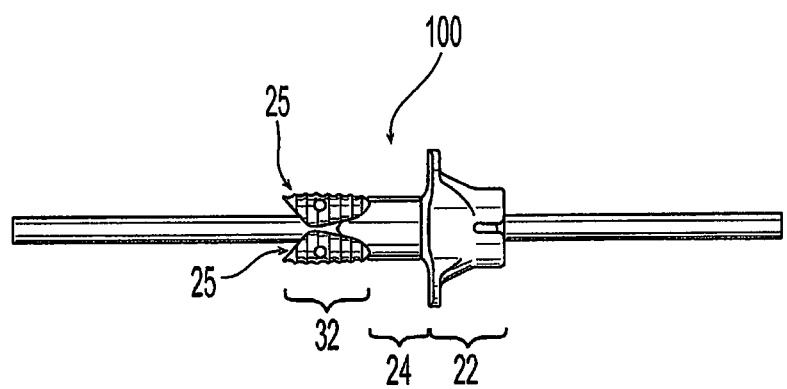
FIGS. 21-22 are side and distal perspective views of another embodiment of an implant according to the invention, shown in a first position extending over a guidewire.
Figure 22:
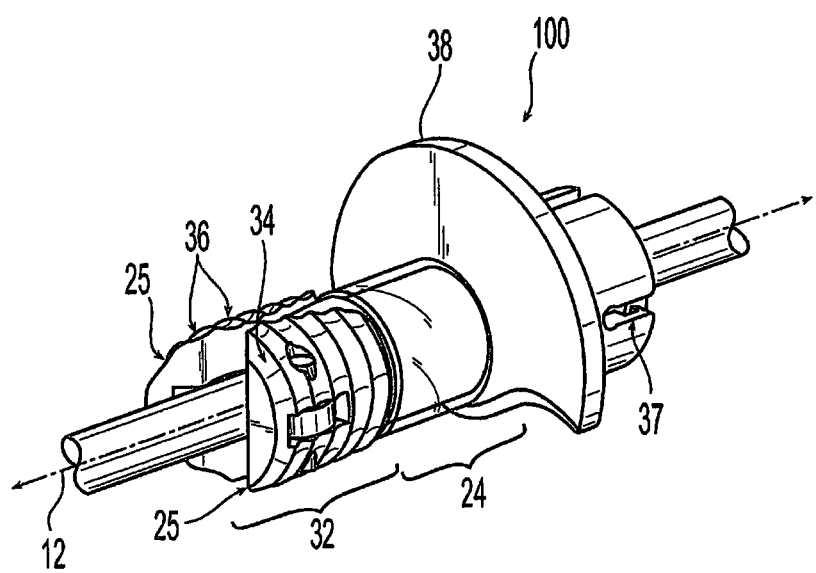
Figure 23:
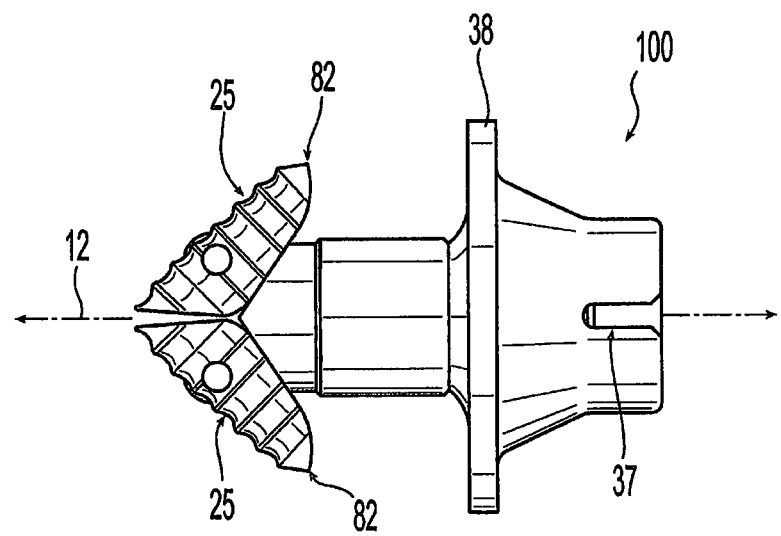
FIGS. 23-24 are side and distal perspective views of the implant of FIG. 21 shown in a second position.
Figure 24:
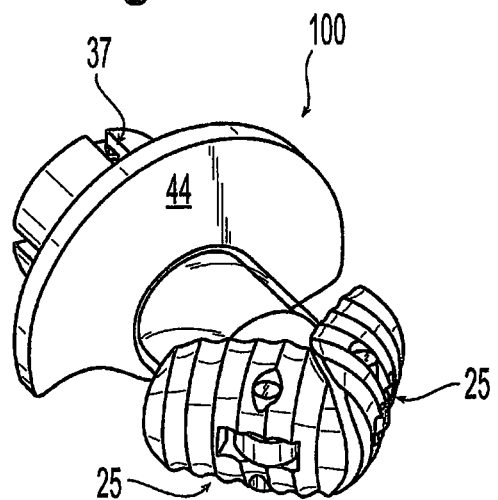
Figure 25:
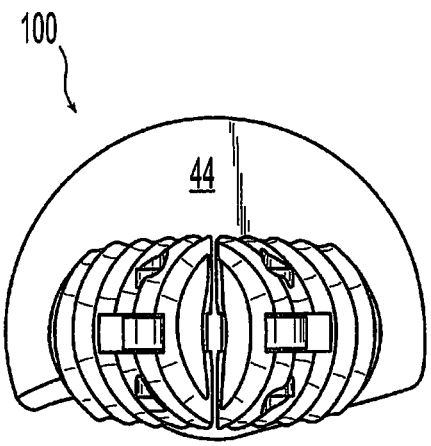
FIGS. 25-26 are proximal perspective and distal end views of the implant of FIG. 21 shown in a second position.
Figure 26:
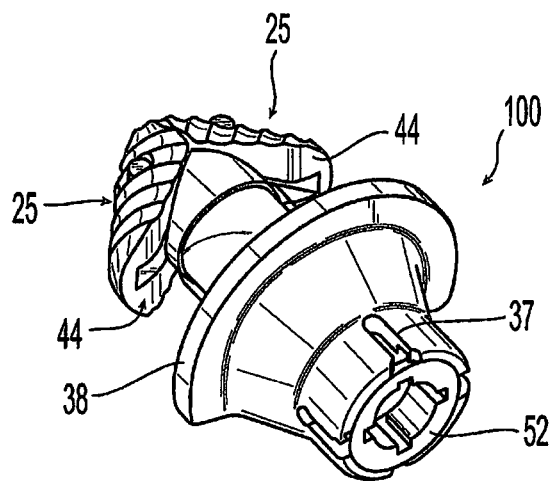
Figure 27:
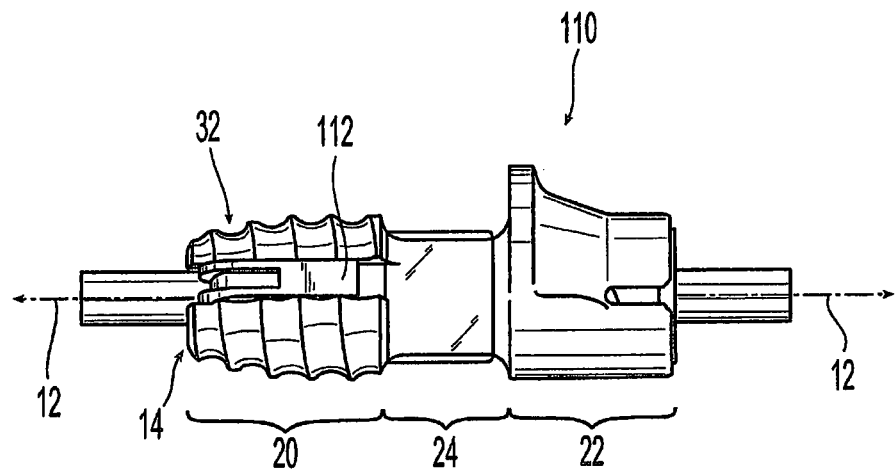
FIGS. 27-28 are side and distal perspective views of another embodiment of an implant according to the invention, shown in a first position extending over a guidewire.
Figure 28:
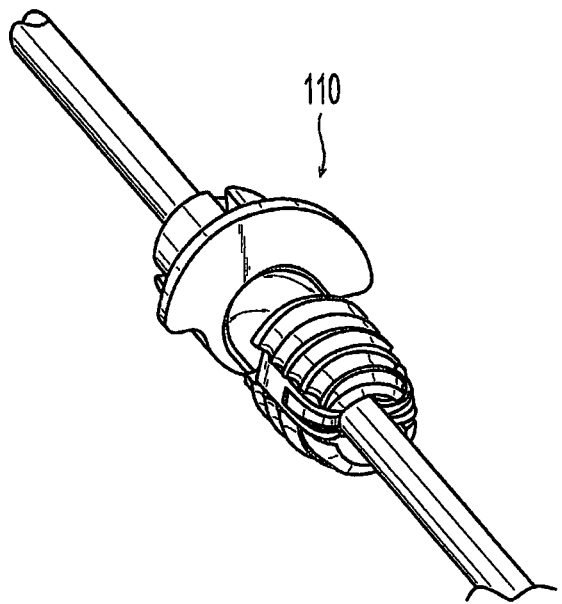
Figure 29:
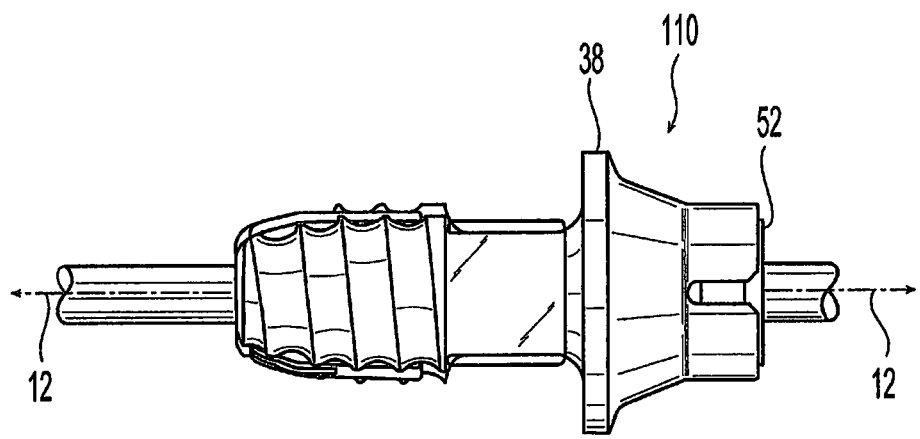
FIGS. 29-30 are side and cross-sectional views of the implant of FIG. 27 shown in a first position.
Figure 30:
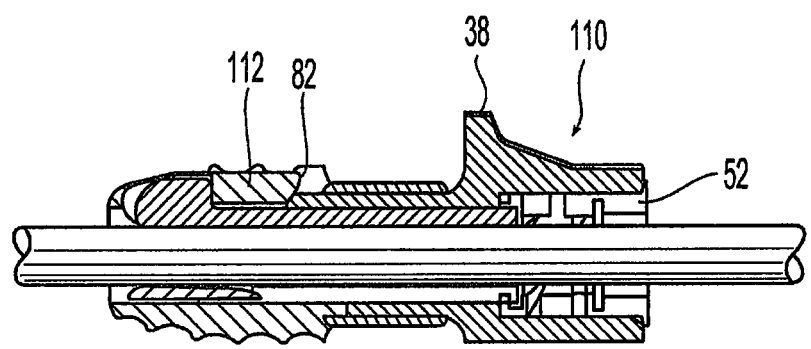
Figure 31:
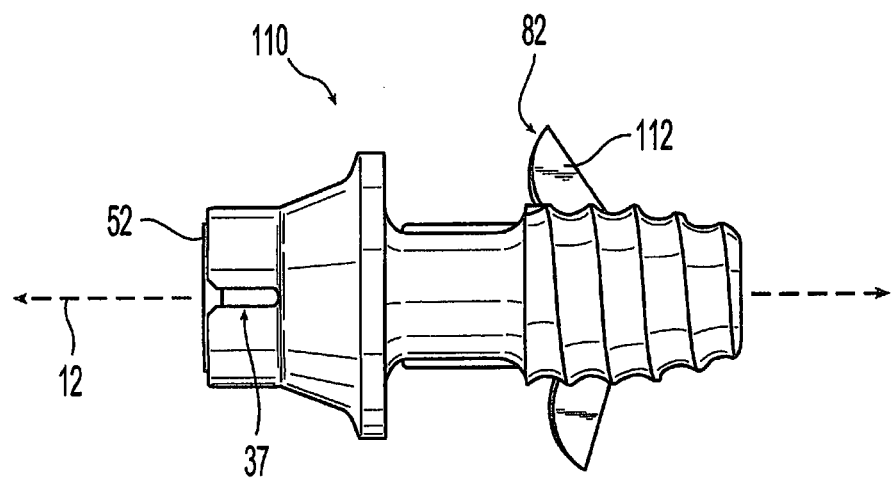
FIGS. 31-32 are side and distal perspective views of the implant of FIG. 27 shown in a second position.
Figure 32:
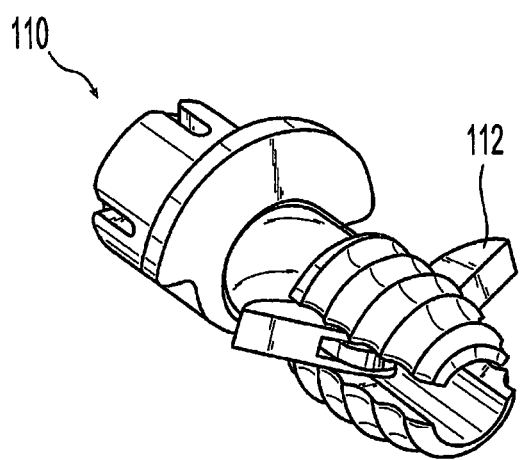
Figure 33:
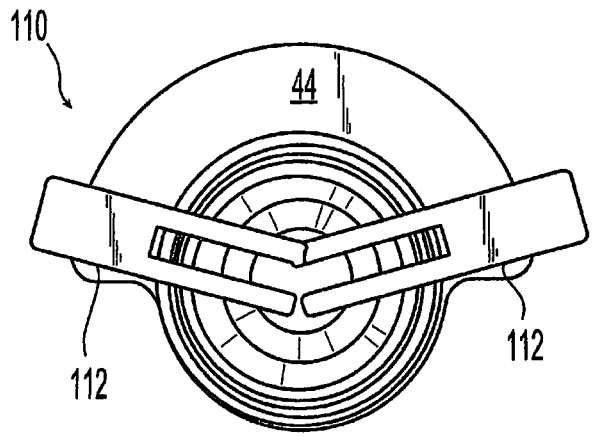
FIGS. 33-34 are distal end and cross-sectional views of the implant of FIG. 26 shown in a second position.
Figure 34:
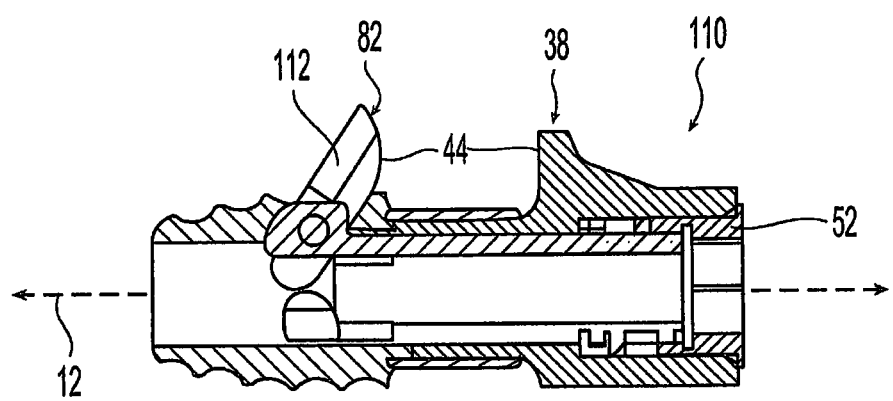

Referring to FIGS. 21-25, another embodiment of an implant 100 according to the invention is shown. Implant 100 is similar to implant 10 described above except wing members 25 may additionally include a ramped, toothed, fluted, threaded or grooved section 32. According to one embodiment, grooved section 32 generally comprises helical or spiral ramp peaks 36 extending from first end toward support portion 24. Ramp peaks 36 of section 32 may have a separation sufficiently narrow to prevent the adjacent spinous process from riding within the grooves 34 defined between the peaks 36. In this regard, when wing members are in the first position, as shown in FIGS. 21-22, the peaks 36 may be configured and dimensioned to engage or contact a portion of the spinous process bone and cause the implant 100 to advance or travel along axis 12 when implant 100 is rotated. In one variation, distraction portion 20 is configured and dimensioned such that when implant 100 is rotated about axis 12, the adjacent spinous processes ride upon ramp peaks 36 and are distracted or separated apart as implant 10 is advanced laterally along axis 12 during implantation. The rate at which the distraction occurs may be readily controlled by a surgeon by controlling the rate of rotation of implant 10, so that the surgeon may advance implant 100 along axis 12 as slow or as fast as desired. In this regard, implant 100 may be characterized as self-distracting, as the implant itself distracts or separates the spinous processes as it is being implanted, i.e. without requiring an additional distraction step or device.

Referring to FIGS. 23-26, implant 100 is shown with wing members 25 in a second or expanded condition. Similar to implant 10, described above, once the implant is laterally advanced to a desired installation position, the flange 38 of trailing end portion 22 may contact and/or abut the lateral side of the spinous processes to prevent further lateral translation and rotation insert 52 of implant 100 may be subsequently rotated about one quarter turn or about 90 degrees to deploy the wing members 25 into the second position as shown in FIGS. 23-26. In this regard, in the final implantation position, the shoulder wall sections 44 may contact the lateral sides of the spinous processes to limit or block movement of the implant along axis 12 and/or dislodgement from the interspinous space. As with implant 10 described above, once the implant is implanted and after the spinous processes are fitted into the central support portion 24, the implant may maintain the spinous processes in a distracted or spaced condition, for example where the distance (a) of the implant is greater than a pre-implantation distance between the spinous processes. Also as described above, the wing members 25 swing outward with the tips 82 generally moving away from the center of the implant. In this regard, the tips 82 are generally configured to move up and under any tissue or muscle that may be abutting against the adjacent spinous processes.

Referring now to FIGS. 27-34, another embodiment of an interspinous process implant 110 is shown. Implant 110 is similar to implant 100 described above, however, in this embodiment, a pair of thin slidable wing fingers 112 are provided within the distraction portion 20. Like implant 100 described above, distraction portion 20 comprises a include a ramped, toothed, fluted, threaded or grooved section 32 disposed about axis 12 and extending from a narrow first end 14 toward central support portion 24. In this embodiment, wing fingers 112 are movable from a first position, shown in FIGS. 27-30, to a second position, shown in FIGS. 31-34. Referring to FIGS. 27-30, wing fingers 112 are depicted in a first or closed position and are configured and dimensioned to facilitate lateral insertion between adjacent spinous processes. In the first position, the exterior of wing fingers 112 are generally recessed within distraction portion 20. One skilled in the art may appreciate that with the wing fingers in the first, or closed, position, such a configuration may facilitate unilateral insertion between adjacent spinous processes.

Referring to FIGS. 31-34, implant 110 is shown with wing fingers 112 in a second position. Similar to implants 10 and 100, described above, once the implant is laterally advanced to a desired installation position, the flange 38 of trailing end portion 22 may contact and/or abut the lateral side of the spinous processes to prevent further lateral translation and rotation insert 52 of implant 110 may be subsequently rotated about one quarter turn or about 90 degrees to deploy the wing fingers 112 into the second position as shown in FIGS. 31-34. In this regard, in the final implantation position, the shoulder wall sections 44 may contact the lateral sides of the spinous processes to limit or block movement of the implant along axis 12 and/or dislodgement from the interspinous space. Also, once the implant is implanted and after the spinous processes are fitted into the central support portion 24, the implant may maintain the spinous processes in a distracted or spaced condition, for example where the distance (a) of the implant is greater than a pre-implantation distance between the spinous processes. As with implants 10 and 100 described above, the wing fingers 112 swing outward with the tips 82 generally moving away from the center of the implant. In this regard, the tips 82 are generally configured to move up and under any tissue or muscle that may be abutting against the adjacent spinous processes.

Figure 35:
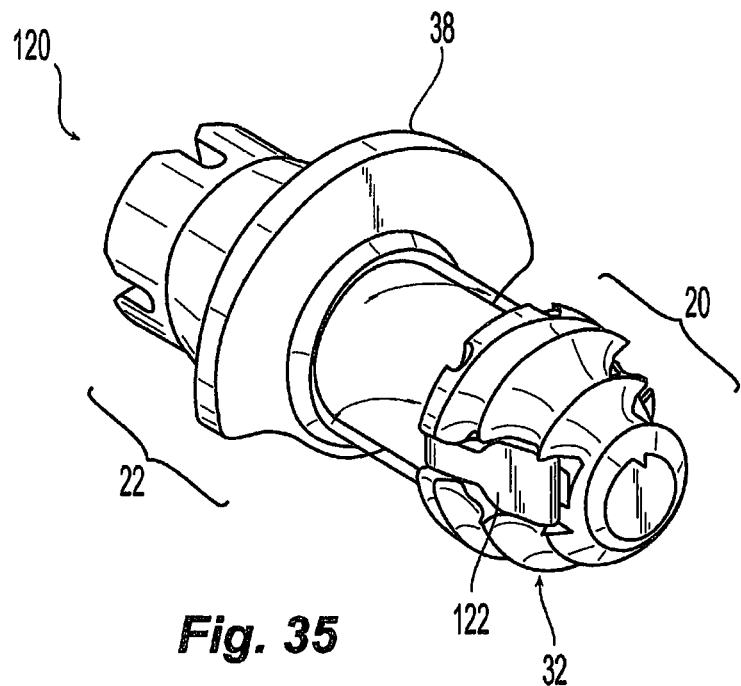
FIG. 35 is a distal perspective view of another embodiment of an implant according to the invention, shown in a first position.
Figure 36:
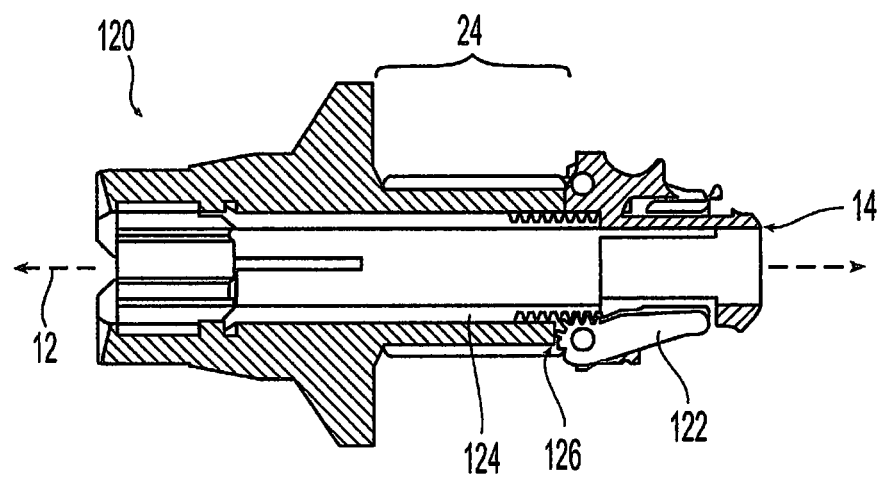
FIG. 36 is a cross-sectional view of the implant of FIG. 35.

Referring now to FIGS. 35-38, another embodiment of an interspinous process implant 120 is shown. Implant 120 is similar to implant 110 described above, however, in this embodiment, a pair of wing fingers or tabs 122 are actuatable by a rotatable gear barrel insert 124. Barrel insert 124 has a worm gear adjacent its distal portion that is configured and dimensioned to engage teeth or prongs 126 on the interior of tabs 122. When barrel insert 124 is rotated, tabs 122 may swing inward toward the second position shown in FIGS. 37-38. Like implant 100 described above, distraction portion 20 comprises a include a ramped, toothed, fluted, threaded or grooved section 32 disposed about axis 12 and extending from a narrow first end 14 toward central support portion 24. In this embodiment, wing tabs 122 are movable from a first position, shown in FIGS. 35-36, to a second position, shown in FIGS. 37-38. Referring to FIGS. 35-36, wing tabs 122 are depicted in a first or closed position and are configured and dimensioned to facilitate lateral insertion between adjacent spinous processes. In the first position, the exterior of wing tabs 122 are generally recessed within distraction portion 20. One skilled in the art may appreciate that with the wing fingers in the first, or closed, position, such a configuration may facilitate unilateral insertion between adjacent spinous processes.

Figure 37:
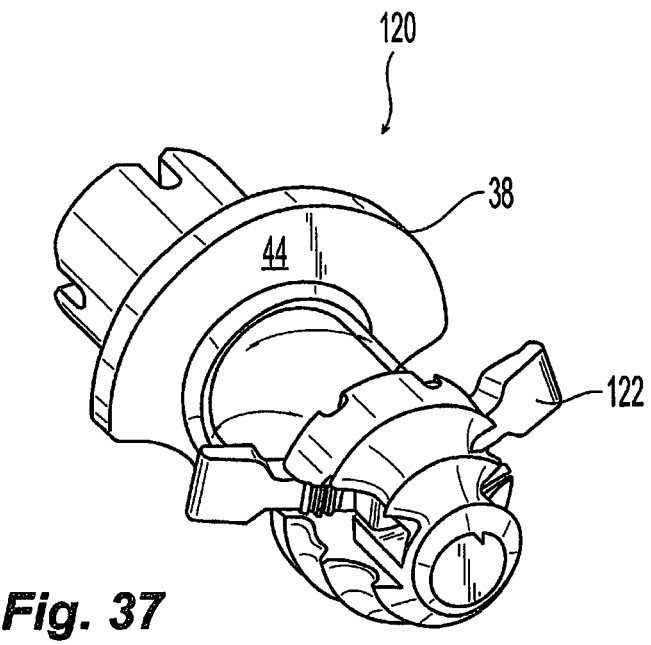
FIG. 37 is a distal perspective view of the implant of FIG. 35, shown in a second position.
Figure 38:
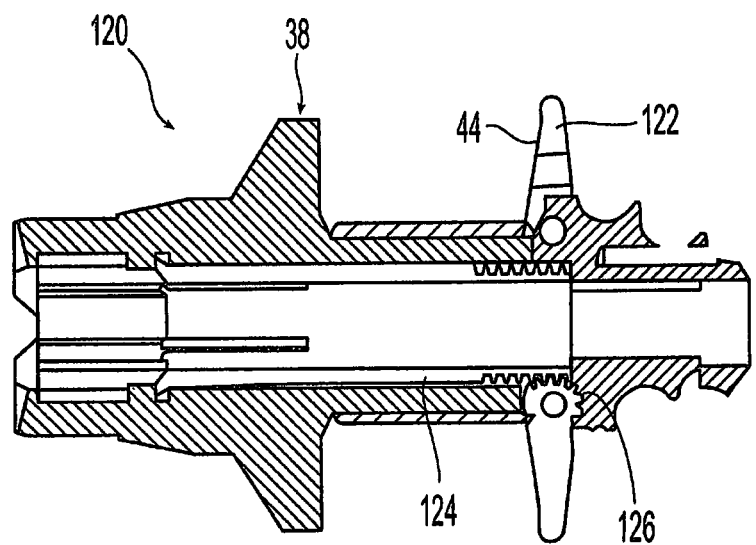
FIG. 38 is a cross-sectional view of the implant as depicted in FIG. 37.

Referring to FIGS. 37-38, implant 120 is shown with wing tabs 122 in a second position. Once the implant is laterally advanced to a desired installation position, the flange 38 of trailing end portion 22 may contact and/or abut the lateral side of the spinous processes to prevent further lateral translation. Barrel insert 124 of implant 120 may be subsequently rotated to deploy the wing tabs 122 into the second position as shown in FIGS. 37-38. In this regard, in the final implantation position, the shoulder wall sections 44 may contact the lateral sides of the spinous processes to limit or block movement of the implant along axis 12 and/or dislodgement from the interspinous space. Also, once the implant is implanted and after the spinous processes are fitted into the central support portion 24, the implant may maintain the spinous processes in a distracted or spaced condition, for example where the distance (a) of the implant is greater than a pre-implantation distance between the spinous processes. When barrel insert 124 is rotated, tabs 122 may swing inward toward the center of the implant.

Figures 39, 40:
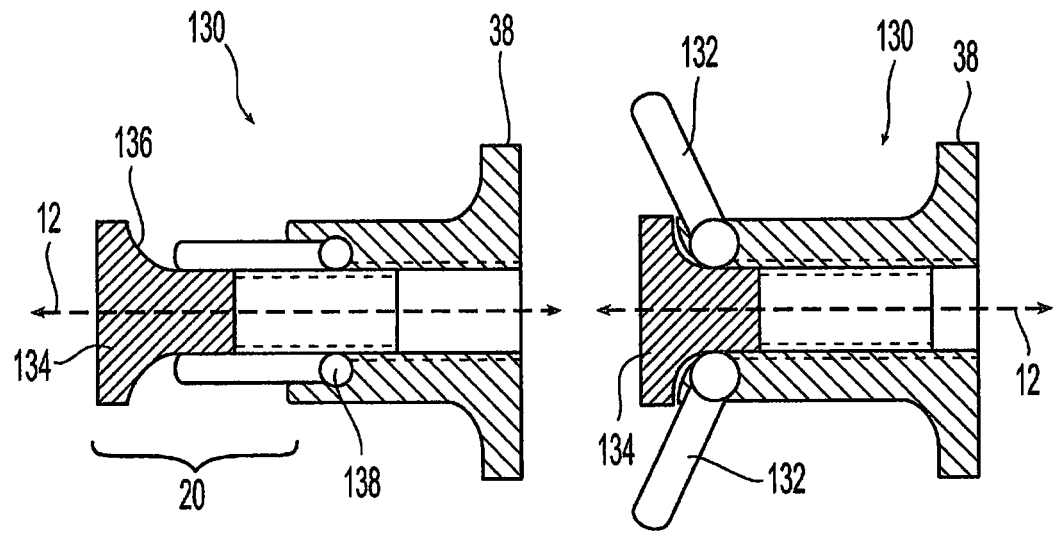
FIG. 39-40 are cross-sectional views of another embodiment of an implant according to the invention, shown in first and second positions, respectively.
Figure 41:
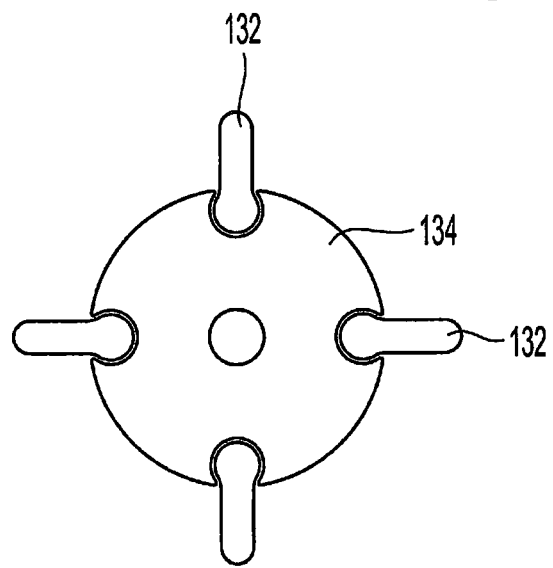
FIG. 41 is a distal end view of the implant of FIG. 40.

Referring now to FIGS. 39-41, another embodiment of an interspinous process implant 130 is shown. Implant 130 is similar to previously described implants, however, in this embodiment, a plurality of thin fingers 132 are provided within the distraction or distal portion 20. In one variation, fingers 132 are pivotably installed adjacent distal portion 20. As best seen in FIGS. 39-40, fingers 132 may be actuated or moved from a first position (FIG. 39) to a second position (FIG. 40) by drawing a front or distal end portion 134 backward in a proximal direction along axis 12. In this regard, an internal ramp portion 136 may be provided to engage a tip portion of fingers 132 such that as the distal end is drawn back, fingers 132 pivot or rotate about their base 138. Similar to previously described embodiments, in a first position, fingers 138 are recessed within distal portion 20 and in a second position, fingers 132 extend outward to create a wall section to limit or block movement of the implant along axis 12 and/or dislodgement from the interspinous space.

Figure 42:
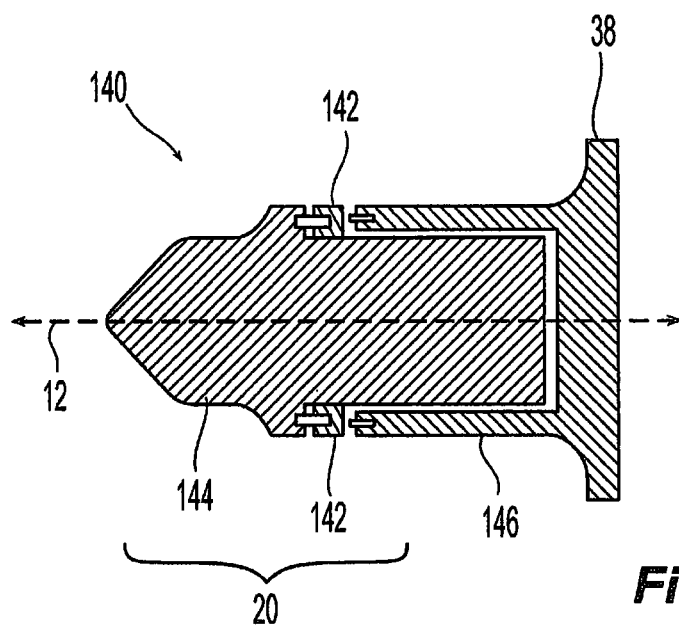
FIG. 42 is a cross-sectional view of another embodiment of an implant according to the invention, shown in a first position.
Figure 43:
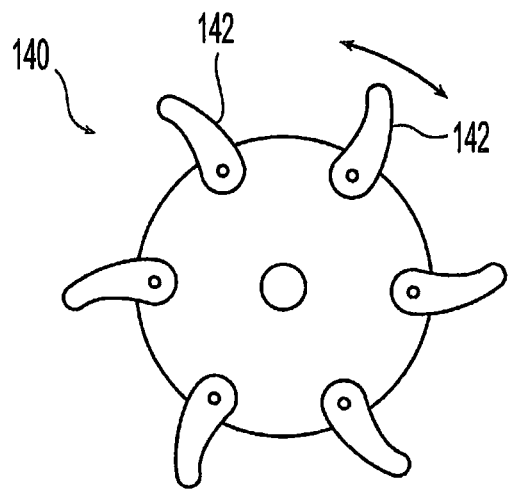
FIG. 43 is a distal end view of the implant of FIG. 42, shown in a second position.
Figure 44:
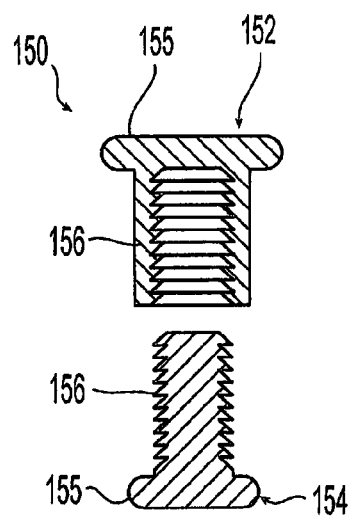
FIGS. 44-45 are cross-sectional and perspective views of a portion of another embodiment of an implant according to the invention.
Figure 45:
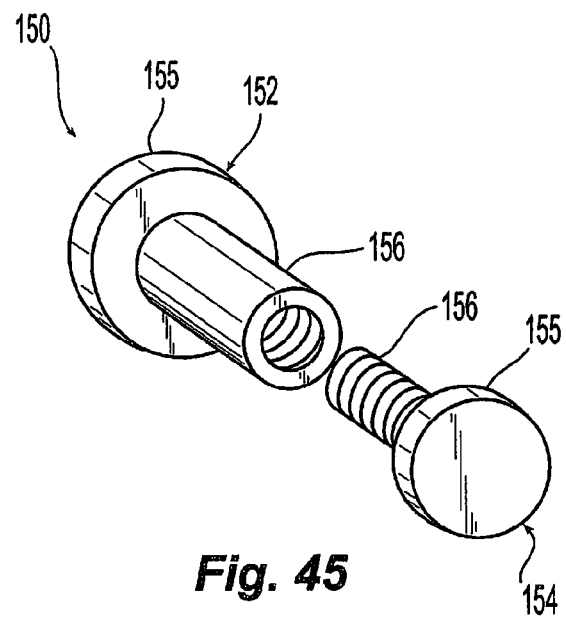
Figure 46:
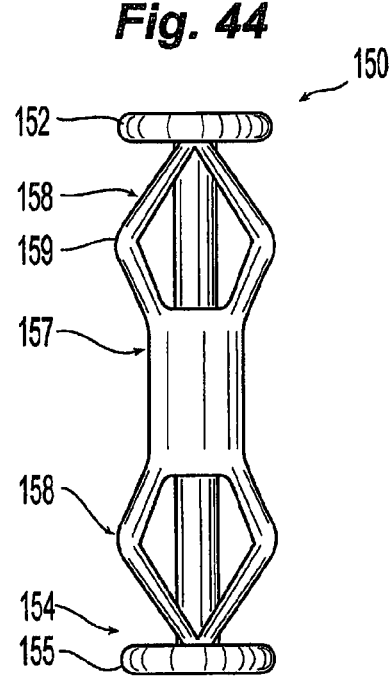
FIGS. 46-47 are side views of the implant of FIGS. 44-45 shown in first and second positions, respectively.

Referring now to FIGS. 42-43, another embodiment of an interspinous process implant 140 is shown. Implant 140 is similar previously described embodiments, however, in this embodiment, a plurality of wing members 142 are pivotably mounted to a distal portion 144. Wing members 142 are configured to remain recessed within distraction portion 20 in a fist position (FIG. 42). Wing members 142 are rotatable about an axis parallel to axis 12 and may be actuated by rotating the central body 146 with respect to distal portion 144. When central body 146 is rotated, wing members 142 swing radially outward toward the second position shown in FIG. 43.

Figure 47:
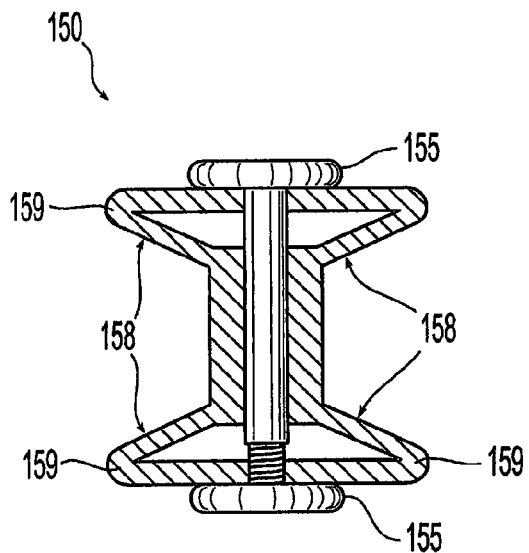

Referring now to FIGS. 44-47, another embodiment of an interspinous process implant 150 is shown. Implant 150 generally comprises first and second members 152, 154 having a shoulder or larger sized diameter portion 155 adjacent a generally cylindrical midsection 156. In one variation, the first and second members may be threadably connectable. In alternate embodiments, first and second members 152, 154 may snappably connectable. A deformable wing body 157 may be disposed about the first and second members 152, 154 and wing body 157 may have bendable ends 158 having one or more flexible joints 159 thereon. First and second members may be concentrically connected at midsection 156 such that the first and second members may be axially moveable with respect to each other such that first and second members 152, 154 may be moved relative to each other form a first position (FIG. 46) to a second position (FIG. 47) to contract or shorten the overall length of implant 150. In this regard, when in the second position as shown in FIG. 47, bendable ends 158 hinge or bend at joints 159 and extend radially outward in a direction transverse to axis 12 toward the second position shown in FIG. 47. Similar to previously described embodiments, in a first position, bendable ends 158 are retracted and in a second position, ends 158 extend outward to create a wall section to limit or block movement of the implant along axis 12 and/or dislodgement from the interspinous space.

Figure 49:
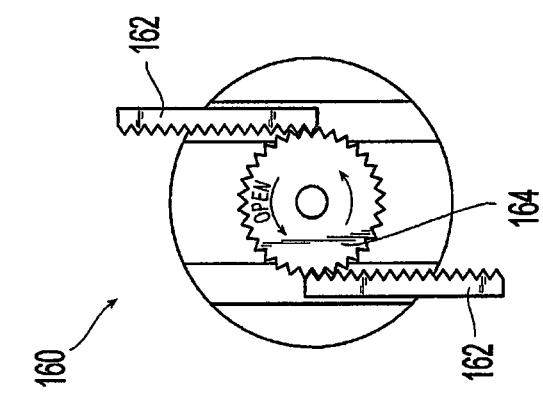
FIGS. 48-49 are end views of another embodiment of an implant according to the invention, shown in first and second positions, respectively.
Figure 48:
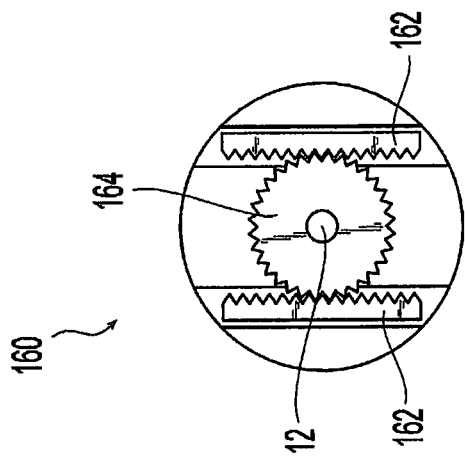

Referring now to FIGS. 48-49, another embodiment of an interspinous process implant 160 is shown. Implant 160 is similar previously described embodiments, however, in this embodiment a pair of geared pins 162 are actuatable by a rotatable gear barrel insert 164. Barrel insert 164 has a gear teeth profile adjacent its distal portion configured and dimensioned to engage corresponding teeth or prongs on the interior of pins 162. When barrel insert 164 is rotated, pins 162 extend radially outward in a direction transverse to central axis 12 toward the second position shown in FIG. 49.

According to certain embodiments of the invention, the implants described above may have a trailing end portion 22 with an external hexagonal shaped portion to engage an installation tool such as a hexagonal socket shaped driver tool. In alternate embodiments, however, any other known rotational and/or driving tools and engagement means may also be used.

Kits having at least one implant such as those depicted in FIGS. 11-15, may include various sizes of implants having varying heights (a), widths (d), and overall lengths (e), for example having variations with incremental distances. In one embodiment, a system or kit may be provided that has implants having heights (a) between about 6 mm to about 22 mm. For example, in one variation implants having heights (a) of 8 mm, 10 mm, 12 mm, 14 mm, 16 mm, 18 mm, and 20 mm may be provided. In another variation, a system or kit may be provided that has implants having widths (d) between about 6 mm to about 18 mm. For example, in one variation implants having widths (d) of 8 mm, 12 mm, and 16 mm may be provided. In yet another variation, a system or kit may be provided that has implants having overall lengths (e) between about 20 mm and about 60 mm. For example, in one variation implants having overall lengths (e) of 25 mm and 50 mm may be provided.

Material

Implants in accordance with the present invention may be made of one or more materials suitable for implantation into the spine of a mammalian patient. Materials in accordance with the present invention may be biocompatible with a mammalian patient and/or may have one or more surface coatings or treatments that allow the spacers to be biocompatible. Materials in accordance with the present invention may include one or more materials having sufficient load capability and/or strength to maintain the desired spacing or distraction between spinous processes. Depending on the design employed, certain embodiments may have components or portions made of a material having certain flexibility, as desired for the particular application. Additionally, the materials of the present invention may be made of one or more materials that maintain their composition and shape for as long a time as possible without degrading or decomposing or changing shape, such that replacement of the implant is avoided.

Suitable materials for use in accordance with the present invention would be known to those skilled in the art. Non-limiting examples include one or more materials selected from medical grade metals, such as titanium or stainless steel, biocompatible polymers, such as polyetheretherketone (PEEK), ceramics, deformable materials, bone, allograft, demineralized or partially demineralized bone, allograft ligament, and polyurethane (for example, for portions of the insert where cushioning is desired). Similarly, any fastening devices may be made of materials having one or more of the properties set forth with respect to the implant itself. For example, screws or pins may include titanium and straps may include polyethylene. In some embodiments, primarily radiolucent material may be used. In this regard, radio-opaque material or markers may be used in combination with the radiolucent material to facilitate implantation. Exemplary radio-opaque material includes but is not limited to titanium alloys, tantalum or other known radio-opaque marker material. As indicated above, implants in accordance with the present invention may have one or more portions that may have modified surfaces, surface coatings, and/or attachments to the surface, which may assist in maintaining the spacer in a desired position, for example by friction. Suitable surface modifications, coatings, and attachment materials would be known to those skilled in the art, taking into consideration the purpose for such modification, coating, and/or attachment.

Methods for Treating Stenosis and Methods of Inserting an Implant

Methods are provided for treating spinal stenosis. Methods are also provided for inserting an implant. These methods may include implanting a device to create, increase, or maintain a desired amount of distraction, space, or distance between adjacent first and second spinous processes. The adjacent first and second spinal processes may be accessed by various methods known by practitioners skilled in the art, for example, by accessing the spinous processes from at least one lateral side/unilateral, bilateral, or midline posterior approach.

Certain methods of the present invention include creating an incision in a patient to be treated, dilating any interspinous ligaments in a position in which the implant is to be placed in the patient, sizing the space between adjacent spinous processes (for example using trials), and inserting an implant of the appropriate size between the adjacent spinous processes. Methods of the present invention may include securing the implant to one or more of the spinous processes, to one or more other portions of the patient's spine, and/or to itself such that the implant maintains its position between the spinous processes.

Methods of the present invention may include dilating or distracting the spinous processes apart from one another before sizing and/or before inserting the implant. Methods may vary depending on which implant is being inserted into a patient. For example, certain implants may require distracting the spinous processes apart before inserting the implant, while other implants may themselves dilate or distract the spinous processes while inserting the implant. In embodiments where the implants themselves dilate or distract the spinous process, the implant may have, for example, a predetermined shape to dilate, distract, or otherwise move or separate apart adjacent spinous processes such as a cam or cam-like profile, it may have a distraction device that is deployed, and/or it may have a tapered expander to distract an opening between the adjacent spinous processes or other features to facilitate distraction of the adjacent spinous processes.

According to certain embodiments, spacers may be placed between the spinous processes anterior to the supraspinous ligament, avoiding the nerves in the spinal canal. The procedure may be performed under local anesthesia. According to one method for surgical procedures, in which an implant is being inserted into the lumbar region, the patient may be placed in a left or right lateral decubitus position with the lumbar spine flexed or in another flexed position. According to one method, a surgeon may desire to use fluoroscopy to align in parallel the adjacent vertebral bodies corresponding to the adjacent spinous processes to gauge the desired distraction distance.

According to certain embodiments, one or more probes may be used to locate the space between the spinous processes. Depending on the design of the spacer to be inserted, the space may be widened, for example with a dilator before inserting the implant.

Figure 50:
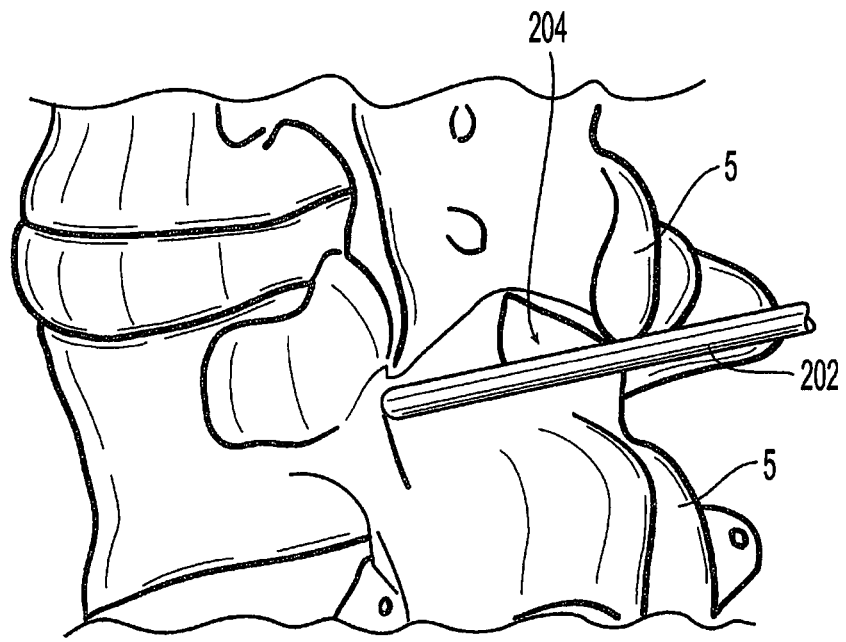
FIGS. 50-56 are perspective views demonstrating various steps according to one embodiment of a method of installation of the implant of FIG. 1.
Figure 51:
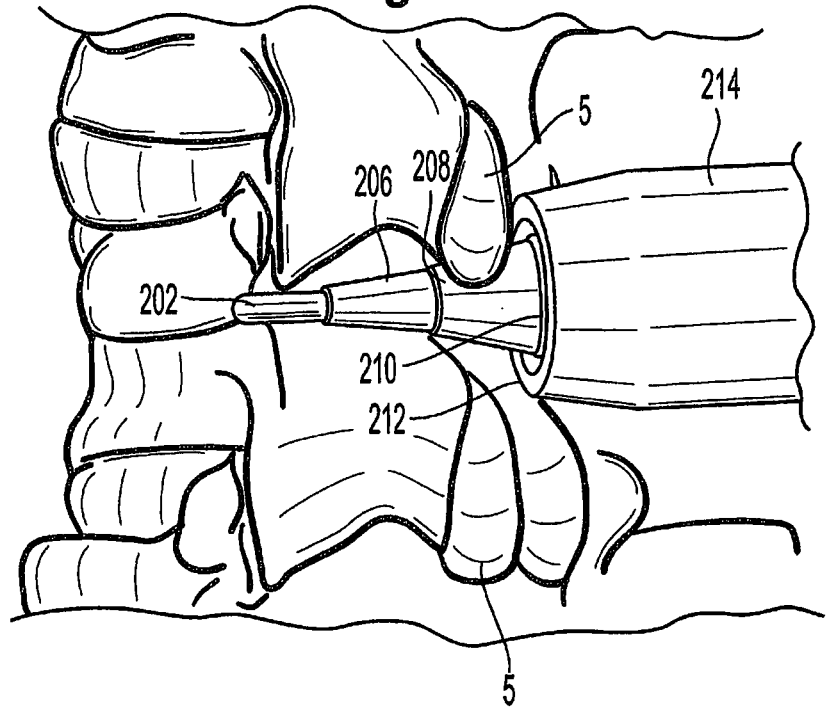
Figure 52:
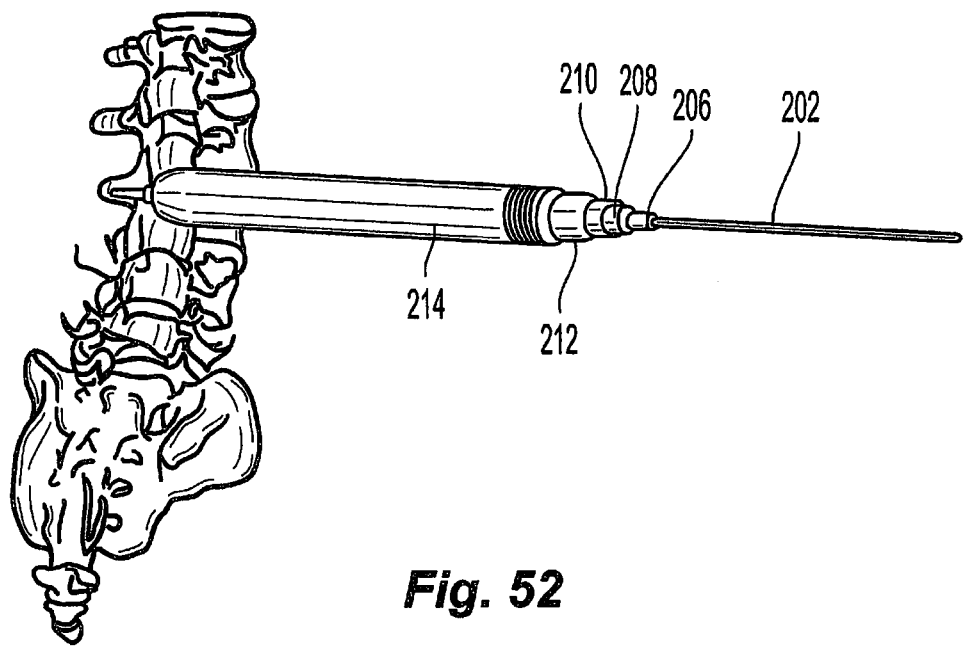
Figure 59:
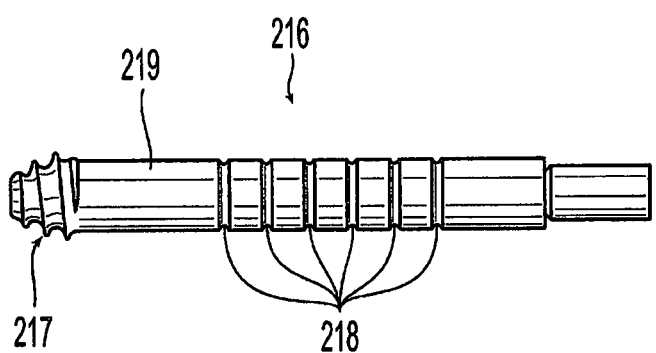
FIG. 59 is a perspective view of one embodiment of a trial instrument according to the invention.
Figure 53:
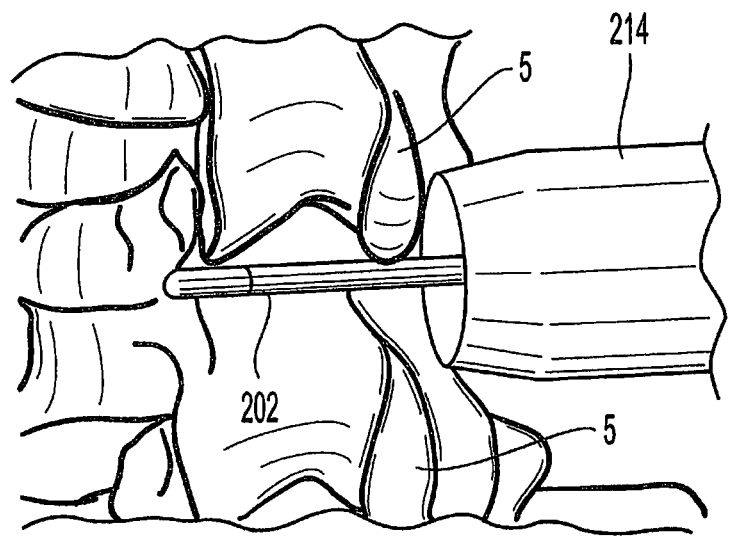
Figure 54:
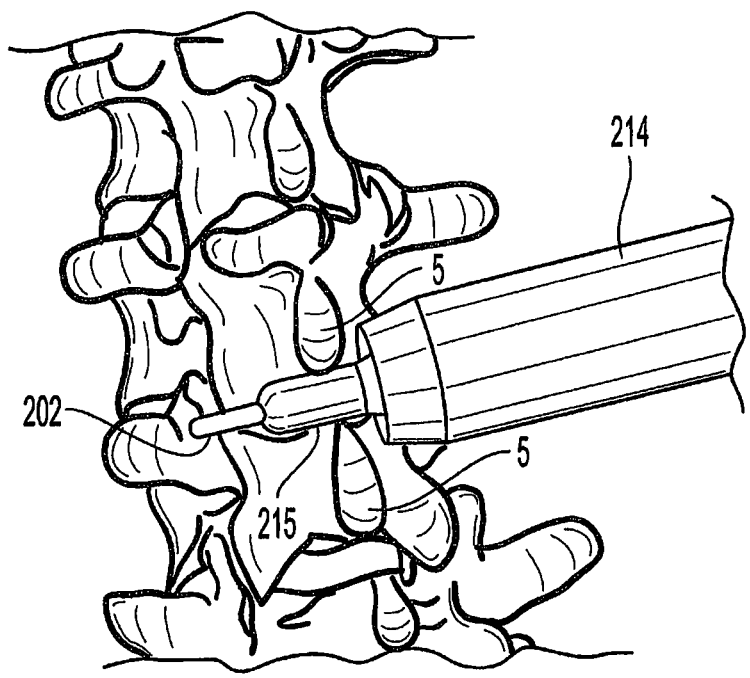

Referring to FIGS. 50-57, one embodiment of a surgical method according to the invention for implanting an implant 10 in the spine is disclosed. According to this embodiment, the adjacent first and second spinal processes 5 may be accessed from one lateral side through a minimally or less invasive procedure. In this regard, according to certain methods of the invention, a unilateral approach may be used to install implant 10 without removal of the supraspinous ligament. In this method, as shown in FIG. 50, a guide wire 202, such as a K wire, is inserted laterally through the skin and into the interspinous space 204. According to one method, a working portal may be created concentric to the guidewire 202, as shown in FIGS. 51-52, by inserting a series of sequentially larger diameter tubes 206, 208, 210, 212, 214 to dilate the tissue surrounding guidewire 202. Referring to FIG. 53, once a dilating tube having a sufficiently large inner diameter to accommodate implant 10 is positioned about guidewire 202, the smaller diameter tubes 206, 208, 210, 212 may be withdrawn, leaving the guidewire 202 and the outer tube 214. Referring to FIG. 54, one or more trials 215 may then be inserted to appropriately size the interspinous space 204 and the trials 215 may also be utilized to dilate interspinous ligaments. In one exemplary embodiment, a generally cannulated cylindrical trial 215, shown in FIG. 54, may be utilized to size the space between adjacent processes 5. Referring to FIG. 59, an alternate embodiment of a trial 216 that may be used is shown which may comprise a ramped tip portion 217 adjacent its distal end and multiple longitudinal indentations or markings 218 on at least a portion of central portion 219 and may provide visual indication when viewed under fluoroscopy of the width of the spinous processes and facilitate the surgeon's selection of an appropriately sized implant. Similarly, the appropriate diameter of central portion 219 of trial 216 may be selected to gauge the amount of distraction desired. In this regard, the spacing of the spinous processes may be viewed under fluoroscopy to facilitate the surgeon's selection of an appropriately sized implant. Finally, an implant of the appropriate size may be inserted between the adjacent spinous processes.

Figure 55:
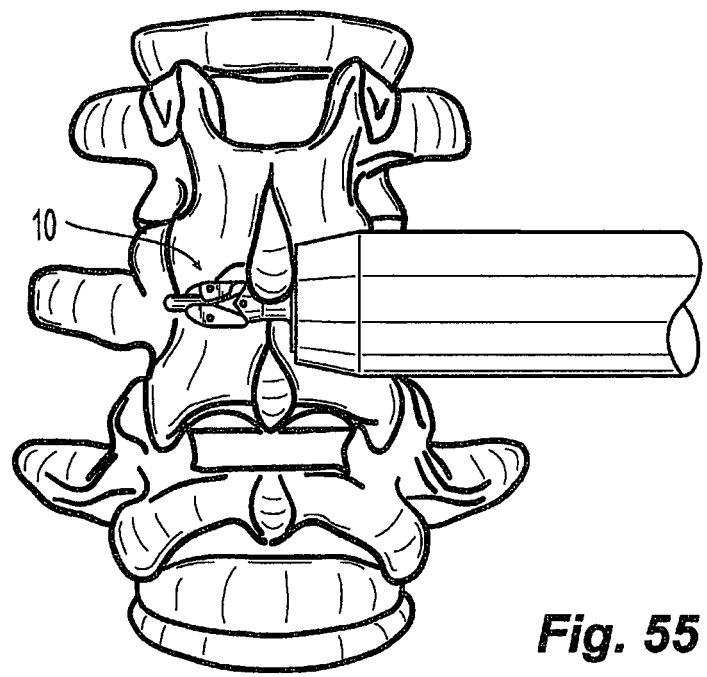
Figure 56:
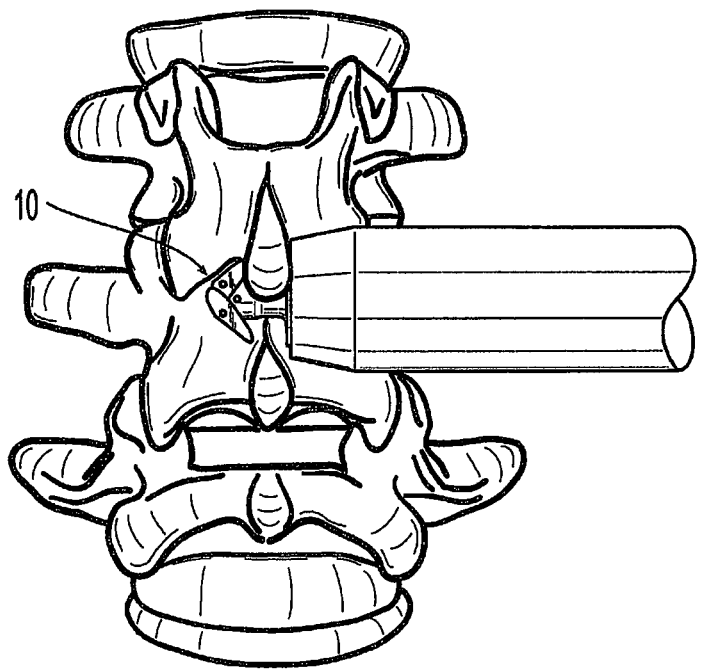

Referring to FIGS. 55-56, one exemplary embodiment of a method of installing implant 10 is shown. Implant 10 is advanced over guidewire 202 through cannulation 18 to the interspinous space 204. During lateral insertion of the implant between the spinous processes, one or more ramp surfaces or portions of the implant may contact one or both of the spinous processes 5 and may initially distract the processes. Implant 10 may be rotated to further advance implant 10 between the spinous processes and, the wedged or tapered shape of the distraction portion 20 may distract the spinous processes further apart from one another, until the implant is rotated and advanced laterally into an implanted position (FIGS. 55-58) with the distraction portion 20 positioned on the contralateral side of the spinous processes and the spinous processes are fitted into the central support portion 24 of the implant 10. Referring to FIGS. 57-58, once implant 10 is installed, the guidewire may be removed through the cannulation leaving the implant 10 in the interspinous space.

While the invention herein disclosed has been described by means of specific embodiments and applications thereof, numerous modifications and variations can be made thereto by those skilled in the art without departing from the scope of the invention.

What is claimed is:

1. A device for implantation in a vertebral column, comprising:
   a body comprising a support portion extending laterally along a lateral axis between first and second end portions;
   wherein at least a portion of the first end portion is moveable from a first position to a second position, wherein in the second position, the portion of the first end portion that is moveable extends beyond the support portion in a direction perpendicular to the lateral axis to a greater extent than in the first position, wherein in the first position the first end portion includes an outer surface and an inner surface that faces a central longitudinal axis of the body;
   wherein the device is configured and dimensioned to be inserted in a position between adjacent spinous processes of the vertebral column, wherein in such a predetermined position, the moveable portion of the front end is moveable from the first position to the second position;
   wherein when in the first position the first end portion comprises a ramp on at least a portion of the outer surface configured and dimensioned to engage and separate the adjacent spinous processes when inserted; and
   when in the second position the first end portion comprises a sidewall on at least a portion of the inner surface, wherein the sidewall is configured and dimensioned to engage a lateral surface of the adjacent spinous processes to limit lateral movement with respect thereto,
   wherein when in the first position, the sidewall of the first end portion faces the lateral axis of the body and in the second position, the sidewall of the first end portion faces the second end portion.

2. The device of claim 1, wherein the body is generally solid.

3. The device of claim 1, wherein the body is cannulated.

4. The device of claim 1, wherein at least a portion of the second end portion extends beyond the support portion in a direction perpendicular to the lateral axis.

5. The device of claim 1, wherein the body is made from a polyetheretherketone (PEEK) material.

6. The device of claim 1, wherein the first end portion comprises a generally frustoconical shape.

7. The device of claim 1, wherein the ramp is helically shaped.

8. The device of claim 1, wherein the ramp is linearly shaped.

* * * * *